US011912743B2

United States Patent
Nicosia et al.

(10) Patent No.: US 11,912,743 B2
(45) Date of Patent: Feb. 27, 2024

(54) COMPOSITITION AND USES OF TELEOST INVARIANT CHAIN TO ENHANCE T CELL RESPONSE TO A VACCINE

(71) Applicant: NOUSCOM AG, Basel (CH)

(72) Inventors: Alfredo Nicosia, Basel (CH); Elisa Scarselli, Basel (CH); Armin Lahm, Basel (CH); Antonella Folgori, Basel (CH)

(73) Assignee: NOUSCOM AG, Basel (CH)

( * ) Notice: Subject to any disclaimer, the term of this patent is extended or adjusted under 35 U.S.C. 154(b) by 299 days.

(21) Appl. No.: 16/761,004

(22) PCT Filed: Nov. 2, 2018

(86) PCT No.: PCT/EP2018/080027
§ 371 (c)(1),
(2) Date: May 1, 2020

(87) PCT Pub. No.: WO2019/086615
PCT Pub. Date: May 9, 2019

(65) Prior Publication Data
US 2021/0363201 A1 Nov. 25, 2021

(30) Foreign Application Priority Data

Nov. 3, 2017 (EP) .................................. 17200036
Dec. 29, 2017 (EP) .................................. 17211235

(51) Int. Cl.
*C07K 14/46* (2006.01)
*A61P 35/00* (2006.01)
(Continued)

(52) U.S. Cl.
CPC ........ *C07K 14/461* (2013.01); *A61K 39/0011* (2013.01); *A61K 39/385* (2013.01);
(Continued)

(58) Field of Classification Search
CPC ...................... C12N 15/86; C12N 7/00; C12N 2710/10343; A61P 35/00; A61K 39/0011;
(Continued)

(56) References Cited

U.S. PATENT DOCUMENTS

2016/0304582 A1* 10/2016 Hill ........................... C12N 7/00
2020/0230220 A1*  7/2020 Nicosia .............. A61K 39/0011

FOREIGN PATENT DOCUMENTS

WO      2010/057501 A1    5/2010
WO      WO-2010057501 A1 * 5/2010 ............. A61K 39/00
(Continued)

OTHER PUBLICATIONS

Arandjelovic S and Ravichandran KS, "Phagocytosis of apoptotic cells in homeostasis", Sep. 2015, Nature Immunology, 16:9, p. 907-917. (Year: 2015).*
Shimizu et al., "Cell-free translation reconstituted with purified components", Aug. 2001, Nature Biotechnology, 19, p. 751-755. (Year: 2001).*
(Continued)

*Primary Examiner* — Gary B Nickol
*Assistant Examiner* — Amelia Nicole Dickens
(74) *Attorney, Agent, or Firm* — McDonnell Boehnen Hulbert & Berghoff LLP

(57) ABSTRACT

Polypeptides comprising a fragment of a teleost invariant chain fused to one or more antigens can enhance T cell response. Alternatively a teleost invariant chain fused to one or more antigens or antigenic fragments thereof can be used. A polynucleotide encoding such polypeptides, vectors comprising such polynucleotides, collection of vectors comprising such polynucleotides are also disclosed. The use of such polypeptides, polynucleotides, vectors for treating or preventing diseases, in particular tumor diseases are also encompassed by the present invention. The teleost invariant chain polypeptides or fragments thereof act as "T cell
(Continued)

Figure 1:
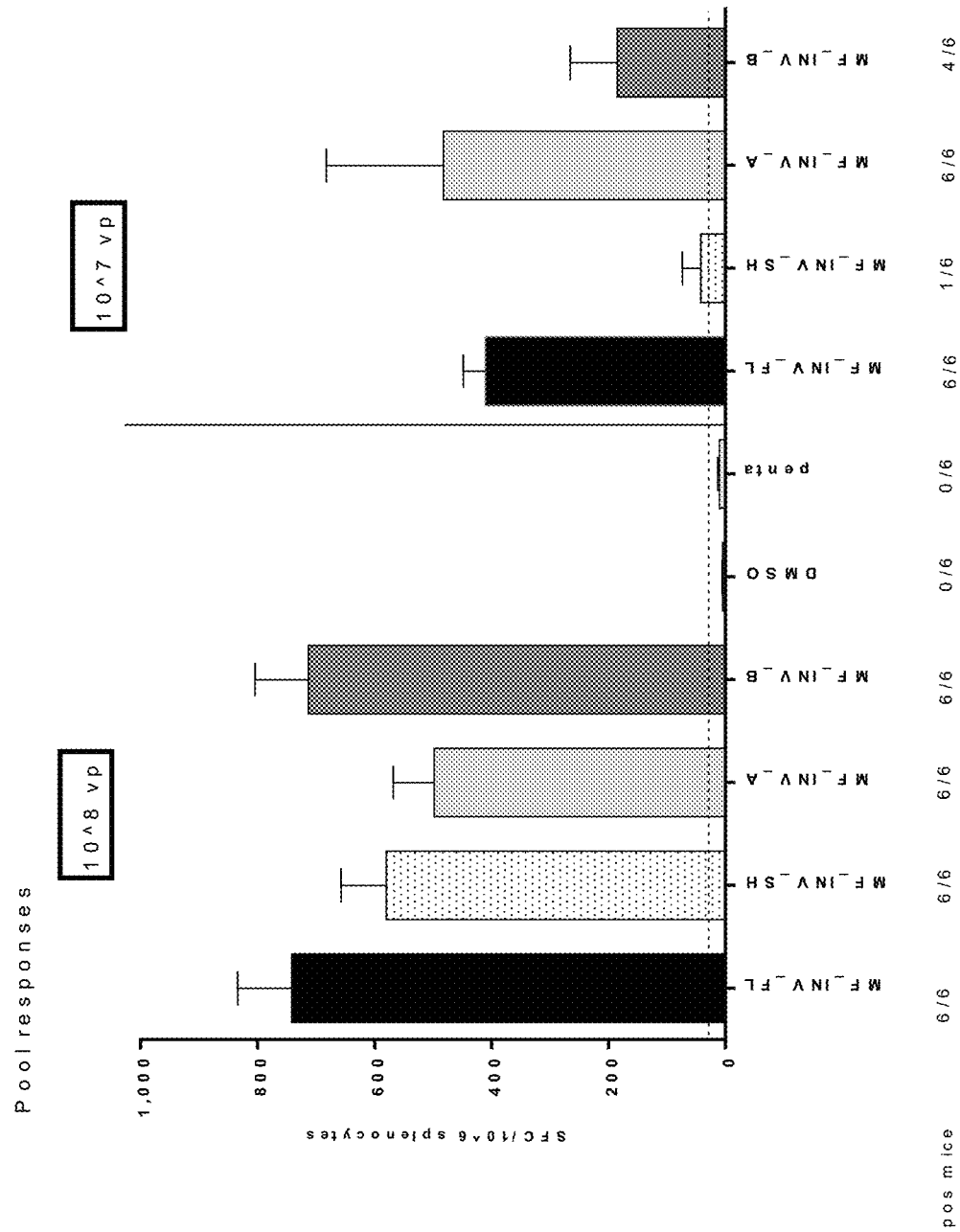

enhancer" converting non-immunogenic antigenic sequences into immunogenic T cell antigens.

9 Claims, 3 Drawing Sheets

Specification includes a Sequence Listing.

(51) Int. Cl.
    *A61K 39/00*     (2006.01)
    *A61K 39/39*     (2006.01)
    *C12N 15/86*     (2006.01)
    *A61K 38/00*     (2006.01)
    *A61K 39/385*     (2006.01)
    *C12N 7/00*     (2006.01)

(52) U.S. Cl.
    CPC ............. *A61K 39/39* (2013.01); *A61P 35/00* (2018.01); *C12N 7/00* (2013.01); *C12N 15/86* (2013.01); *A61K 38/00* (2013.01); *A61K 2039/53* (2013.01); *A61K 2039/6031* (2013.01); *A61K 2039/70* (2013.01); *C07K 2319/03* (2013.01); *C07K 2319/40* (2013.01); *C12N 2710/10343* (2013.01); *C12N 2710/10371* (2013.01)

(58) Field of Classification Search
    CPC .......... A61K 2039/6031; A61K 39/385; A61K 39/39; A61K 2039/53; A61K 2039/70; C01K 14/461; C07K 2319/03; C07K 2319/40; C07K 14/461
    See application file for complete search history.

(56) References Cited

FOREIGN PATENT DOCUMENTS

| WO | 2012/141984 | A1 | | 10/2012 | |
|---|---|---|---|---|---|
| WO | 2015/082922 | | | 6/2015 | |
| WO | WO-2019012091 | A1 | * | 1/2019 | ......... A61K 39/0011 |

OTHER PUBLICATIONS

Li et al. "Identification of cathepsin B from large yellow croaker (*Pseudosciaena crocea*) and its role in the processing of MHC class II-associated invariant chain", Apr. 2014, Developmental and Comparative Immunology, 45, p. 313-320. (Year: 2014).*
"Thereof Definition" Accessed Nov. 4, 2022, Cambridge English Dictionary, p. 1-4. (Year: 2022).*
"Amino Acid Structure" Accessed Nov. 3, 2022, ChemTalk, p. 1-11. (Year: 2022).*
Zhou et al. "Analysis of the transcriptomic profilings of Mandarin fish (*Siniperca chuatsi*) infected with Flavobacterium columnare with an emphasis on immune responses", Dec. 2014, Fish & Shellfish Immunology, 43, p. 111-119. (Year: 2015).*
Capone, Stefania et al. "Fusion of HCV nonstructural antigen to MHC class !!-associated invariant chain enhances T-cell responses induced by vectored vaccines in nonhuman primates" Molecular Therapy, The Journal of the American Society of Gene Therapy (2014) vol. 22(5), pp. 1039-1047.
Spencer, Alexandra et al. "Enhanced vaccine-induced CD8+ T cell responses to malaria antigen ME-TRAP by fusion to MHC class ii invariant chain" Plos One (2014) vol. 9(6), pp. e-1100538.
The International Search Report (ISR) with Written Opinion for PCT/EP2018/080027 dated Feb. 6, 2019, pp. 1-14.
Van De Ven K. et al., "Targeting the T-cell co-stimulatory CD27/CD70 pathway in cancer immunotherapy: rationale and potential", Immunotherapy, 2015, v. 7(6): 655-667.
Miyata, et al., "Two types of amino acid substitutions in protein evolution." J. Mol Evol., 1979, v. 12: 219-236.
Rosano, et al., "Recombinant protein expression in *Escherichia coli*: advances and challenges," Frontiers in Microbiology, 2014, v. 5 (article 172) 1-17.
A0A0E3JX56_SINCH[online], Jun. 24, 2015.
Spencer, et al. "Enhanced Vaccine-Induced COB+ T Cell Responses to Malaria Antigen ME-TRAP by Fusion to MHC Class II Invariant Chain," Plos One, Jun. 2014, vol. 9, Issue 6, e100538.
Capone, et al., "Fusion of HCV Nonstructural Antigen to MHC Class II-associated Invariant Chain Enhances T-cell Responses Induced by Vectored Vaccines in Nonhuman Primates." Molecular Therapy, May 2014, vol. 22, No. 5, pp. 1039-1047.
Sun and Nie, GenBank: AAS77256.1; MHC II invariant chain [Siniperca chuatsi], Jun. 30, 2004.

* cited by examiner

Fig. 2

```
                                                                           TMD
Monopterus_albus       MADSQEDAPLARGSVAGSEEALVLPVAPRGGSNSR ALKIAGLTTLACLLLASQVFTAYMVF
Oryzias_latipes        MANTAEDASLAAEDVSGSEENLIHRVVHRGGSNSR AFKIAGLTTLACLLLASQVFTAYMVF
Oreochromis_niloticus  MAHSQDDAPLARGSLADSEEILLPPAAPRGGSNSR ALKIAGLTTLACLLVASQVFTAYTVF
Lates_calcarifer       MAHNPEDAPLARGSLAGSEEDLVVPAGPRGGSNSR ALKVAALTTLACLLLSSQVFTAYMVF
Siniperca_chuatsi      MADSAEDAPMARGSLAGSDEALILPAGPTGGSNSR ALKVAGLTTLTCLLLASQVFTAYMVF
Dicentrarchus_labrax   MAHS EDAPLATGSLAGSEEALVLSGRPTGGSNSR ALKIAGLTTLACLLLASQVFTAYMVF MPD
Monopterus_albus       DQKQQIHTLQKNSERMSRQMTRTSQAV APVKMHLPMNSLPMLMDYTSNEDPKETKTPLTKL
Oryzias_latipes        NQKQQIHTLQKSSERMGKQLTRASQAV APARMAMPMNSLPLVSDFSED-----AKTPLTKL
Oreochromis_niloticus  SQKQQIHTLQKNSDRMNKQLTRSSHAV APVRMAMPMNSLPLLMDFTED--STAPKTPLTKL
Lates_calcarifer       SQKQQIHTLQKNSERLGKQMTRSSQAV APVRMQMPMSSLPLMMDFTTDEDTKTSKTPLTKL
Siniperca_chuatsi      GQKEQIHTLQKNSERMSKQLTRSSQAV APMKMHMPMNSLPLLMDFTPNE-D--SKTPLTKL
Dicentrarchus_labrax   GQKEQIHTLQKNSERMTKQLTRSSQAV APVRMHMPMSSLPMLMDFTDED-SKATKTPLTKL
                       ***************

Monopterus_albus       QDTAVVSVEDQLKELIQDAQLPEFNETFMDNMQRLKQLTNDSEWKSFETWMRYWLIFKMSQ
Oryzias_latipes        QNTAVVSVEKQLMDLMQDFSLPKFNETFQANLETLRQQVNESEWQTFETWMRYWLIFQMAQ
Oreochromis_niloticus  QDTAIVSVEKQLMDLMQDSELPQFNETFLANLQTLKQHMNDSEWKSFETWMRYWLIFKMAQ
Lates_calcarifer       QDTAIVSVEKQLKDLLQDAQLPQFNETFQANLQSLKQQINESEWKSFESWMRYWLIFQMAQ
Siniperca_chuatsi      QDTAVVSVEKQLKDLMQDSQLPQFNETFLANLQGLKQQMNESEWKSFESWMRYWLIFQMAQ
Dicentrarchus_labrax   QDT-VVSVEKQVKDLIQDSQLPQFNETFMANLQSLKQHINESEWQSFESWMRYWLIFQMAQ Monopterus_albus       QKPTAPTTEQ---AMTKCQREAKEG---LIGSYKPQCDEQGHYMPMQCWHGTGYCWCVDGS
Oryzias_latipes        KQPPAPTPQPASMIKTKCQLEAAPDTISKIGTYKPQCDEQGKYKAMQCWHATGYCWCVDES
Oreochromis_niloticus  QQPATPTPQSATTIKTKCQVEAGPG-PSKIGSYKPQCDEQGRYKPMQCWHATGYCWCVDGE
Lates_calcarifer       QKPVPPTSQPATKIMTKCQLEAAPG-AGKIGSYKPQCDEQGRYLPMQCWYPTGFCWCVDQT
Siniperca_chuatsi      QKPVPPTADPASLIKTKCQMESAPG-VSKIGSYKPQCDEQGRYKPMQCWHATGFCWCVDET
Dicentrarchus_labrax   KTPVPPTADPASLIKTKCQMEAAPG-PSKIGSYKPQCDEQGRYKPMQCWHATGYCWCVDET Monopterus_albus       GTPIPGTKMRGRPQCPRAT-ASRHAMRSPFLMQRTVGIDDEK--
Oryzias_latipes        GNPIEGTTMRGRPDCRRGL-APYRMMVQPRLMQRTFLDDEKKDK
Oreochromis_niloticus  GHPIEGTTMRGRPDCQRAA-FPRRMMVAPRLMQKTYDMDDEKQK
Lates_calcarifer       GKVIEGTSMRGRPDCQRG--VPRRMMFAPRLMQKTLAVDDE---
Siniperca_chuatsi      GAVIEGTTMRGRPDCQRRALAPRRMAFAPSLMQKTISIDDQ---
Dicentrarchus_labrax   GTAIEGTTMRGRPDCQRGS-MPRRVMLAPRLMQKTLSFDDQ---
```

COMPOSITION AND USES OF TELEOST INVARIANT CHAIN TO ENHANCE T CELL RESPONSE TO A VACCINE

CROSS-REFERENCE TO RELATED APPLICATIONS

This application is a U.S. national phase of International Application No. PCT/EP2018/080027, filed on Nov. 2, 2018, which claims priority to European Patent Application No. 17211235.1, filed Dec. 29, 2017; and European Patent Application No. 17200036.6, filed Nov. 3, 2017, all of which are incorporated by reference herein in their entirety.

BACKGROUND OF THE INVENTION

Sometimes vaccines elicit a suboptimal or no T-cell immune response. This phenomenon of poor induction of T-cell immune response is more frequently observed in case of vaccinations that target antigens that are either fully self molecules, e.g. cancer-specific antigens, or partially self, e.g. cancer-specific neoantigens. Cancer-specific neoantigens mostly derive from point mutations in coding regions of genes, which lead to non-synonymous single nucleotide variants resulting in the change of one amino acid. A single amino acid change in a protein sequence very rarely generates a novel epitope able to induce a potent immune response. In most cases, this small change either does not generate a novel epitope at all or may generate a very weak one. Because of pre-existing central tolerance against self antigens, the induction of potent immune responses against cancer specific antigens through vaccination remains a challenging task. To overcome the lack of or poor immunogenicity of cancer specific antigens and neoantigens, several strategies have been employed to rescue lack/poor immunogenicity of some genetic vaccines. Invariant chain (INV) has been shown to enhance CD8+ T cell induction in the context of genetic vaccination. The invariant chain is a chaperone protein of major histocompatibility complex (MHC) class II molecules, required for their maturation and assembly. INV also plays a role in presenting antigenic peptides and it has been demonstrated to increase induction of T cells when fused to an antigen in the context of genetic vaccination. Improved immunization capacity with a lentiviral vector expressing ovalbumin fused to INV has been described (Rowe et al 2006 Mol Ther 13(2) 310-9). Subsequently, various reports documented enhanced induction of CD8+ T cell responses by human adenovirus 5 and plasmid DNA vectors expressing INV-fused antigens.

In cancer vaccination, it is important to avoid tumor escape through the emergence of novel cancer specific antigens not recognized by vaccine induced T cells. The challenge for a cancer vaccine in curing cancer is to induce a diverse population of immune T cells capable of recognizing and eliminating as large a number of cancer cells as possible at once, to decrease the chance that cancer cells can "escape" the T cell response. Therefore, it is desirable that the vaccine encodes quite a large number of cancer specific antigens. This is particular relevant for the recently described personalized vaccine approach based on cancer specific neoantigens. In order to optimize the probability of success as many neoantigens as possible should be targeted by the vaccine, however the maximal insert size of vectors is limited. Full-length INV sequences or large fragments thereof occupy a relatively large portion of the vaccine antigen insert. Therefore, the use of short polypeptide as T cell enhancer is preferable in the context of anti-cancer vaccination especially when using several cancer specific antigens in the vaccine.

Genetic vaccination platforms based on adenovirus, in particular Great Apes derived Adenovirus (GAd) viral vector were shown to be very potent for induction of T cell responses and Great Ape derived Adenoviruses are suitable for encoding large antigens in the format of artificial genes composed of polynucleotides encoding fragments from different proteins linked one after the other (Borthwick, N., et al., Mol Ther, 2014. 22(2): p. 464-75). Unexpectedly, when used in the context of cancer specific neoantigens, no T cell mediated immune response was induced.

The present inventors identified specific INV sequences able to restore immunogenicity, which are also referred to in the present application as "T cell enhancer amino acid sequence". Such T cell enhancer amino acid sequences were suitable in overcoming the lack of or poor immunogenicity of the cancer specific neoantigens. In particular two short fragments of a non-human Teleostei INV were identified both not including the transmembrane domain that acted as potent T cell enhancers.

The use of human INVs or of INVs of phylogenetically closely related species may result in undesired induction of an immune response against this self sequence in the context of vaccination. The autoimmune response would be in this case directed towards normal tissues in which INV is expressed. The present inventors have surprisingly found that INVs of teleosts although quite different from mammalian INVs increase the T cell response against antigens in mammalians, that this T cell response enhancing effect is exerted on multiple antigens fused to a teleost invariant chain and that already a short fragment of teleost INV is sufficient to elicit this response. Thus, the present invention provides inter alia: (i) an improved enhancer of T cell response against antigens in mammals, with a decreased likelihood of eliciting unwanted T cell responses against healthy tissue, (ii) an enhancer of T cell response against multiple antigens, and (iii) a short fragment capable of eliciting a T cell that maximizes the ability to fuse a large number of antigens or antigenic fragments thereof.

SUMMARY OF THE INVENTION

In a first aspect the present invention provides a polypeptide comprising:
(a) a fragment of an invariant chain (INV) of a Teleostei, which has T cell response enhancer activity, comprising or consisting of between 16 to 27 amino acids of the membrane proximal domain (MPD) of an INV of the Teleostei, wherein the MPD is preferably characterized by the following amino acid sequence:

$X_1QKX_2QIHTLQKX_3SX_4RX_5X_6X_7QX_8TRX_9SX_{10}AV$ wherein
$X_1$ is G, D, S or N;
$X_2$ is E or Q;
$X_3$ is N or S;
$X_4$ is D or E;
$X_5$ is M or L;
$X_6$ is G, N, S or T;
$X_7$ is K or R;
$X_8$ is L or M;
$X_9$ is S, T or A; and
$X_{10}$ is Q or H;
and wherein the 16 to 27 amino acids of the MPD are preferably at least 70% identical to SEQ ID NO: 7;

and optionally one or more antigens or antigenic fragments thereof;
or
(b) a full length Teleostei INV of SEQ ID NO: 1 or a variant thereof, which has T cell response enhancer activity, wherein the amino acid sequence of the MPD of the variant is at least 80% identical to SEQ ID NO: 7 and one or more antigens or antigenic fragments thereof.

In a second aspect the present invention relates to a polynucleotide encoding the polypeptide according to the first aspect of the present invention.

In a third aspect the present invention relates to a vector comprising the polynucleotide according to the second aspect of the invention.

In a fourth aspect the present invention relates to a collection of two or more different vectors, wherein the different vectors each comprise a polynucleotide according to the second aspect of the present invention encoding a different polypeptide according to the first aspect of the present invention.

In a fifth aspect the present invention relates to a pharmaceutical composition comprising the polypeptide of the first aspect of the present invention, a polynucleotide of the second aspect of the present invention or a vector of the third aspect of the present invention or collection of vectors of the fourth aspect of the invention and a pharmaceutically acceptable excipient and optionally one or more adjuvants.

In a sixth aspect the present invention relates to a kit of parts comprising the pharmaceutical composition of the fifth aspect of the present invention and separately packaged at least one immunomodulator, for example a modulator of a checkpoint molecule (MCM), or at least one polynucleotide encoding the immunomodulator, for example a MCM, or a vector comprising the polynucleotide encoding the immunomodulator, for example a MCM.

In a seventh aspect the present invention relates to a polypeptide according to the first aspect of the invention, a polynucleotide according to the second aspect of the invention, or a vector or a collection of vectors according to third or fourth aspect of the invention for use as a medicament.

In an eight aspect the present invention relates to polypeptide according to the first aspect of the invention, a polynucleotide according to the second aspect of the invention, or a vector or a collection of vectors according to third or fourth aspect of the invention, or a pharmaceutical composition according to the fifth aspect of the invention or kits comprising such pharmaceutical compositions according to the sixth aspect of the invention for use in preventing or treating a proliferative disease, preferably cancer, viral disease or bacterial disease.

FIGURE LEGENDS

FIG. 1: Immunogenicity of GAd vectors at doses of $5\times10^7$ viral particles (vp) or $5\times10^8$ vp. Vectors encode for Mandarin Fish INV full length (MF_INV_FL SEQ ID NO: 26), Mandarin Fish INV short version (residue 1 to 81 of SEQ ID NO: 26, MF_INV_SH), Mandarin Fish INV variants A (residue 62 to 88 of SEQ ID NO: 26, MF_INV_A) and B (residue 66 to 81 of SEQ ID NO: 26, MF_INV_B) linked to the CT26 pentatope antigen. Penta represents the CT26 pentatope antigen without the Mandarin Fish INV sequence or a fragment thereof and with only an initial methione. Values reported were obtained by an ELISpot assay on spleen cells of immunized animals. Splenocytes were stimulated ex vivo two weeks post vaccination with a pool of five synthetic peptides corresponding to the sequences of the five cancer specific neoantigens containing the mutation. Responses are expressed as number of T cells producing IFNγ per millions of splenocytes. Shown at the bottom is the number of mice showing a positive response out of a total number of 6 immunized mice for each tested vector construct. The dashed line represents the threshold for a positive response.

FIG. 2: Alignment of invariant chains of various Teleostei species. The first box characterizes the 26 amino acid long transmembrane domain (TMD). The membrane proximal domain (MPD) is immediately C-terminally of the TMD and highlighted with a second box. The location and extend of the short 16 amino acid long invariant chain fragment MF_INV_B comprised in the MPD is highlighted by a series of asterisk (*) below the second box. ML_INV_A corresponds to the entire MPD, as marked on the alignment. The INV sequences are from top to bottom the amino acid sequences according to SEQ ID NO: 3, SEQ ID NO: 6, SEQ ID NO: 4, SEQ ID NO: 5, SEQ ID NO: SEQ ID NO: 1, and SEQ ID NO: 2.

Figure 3:
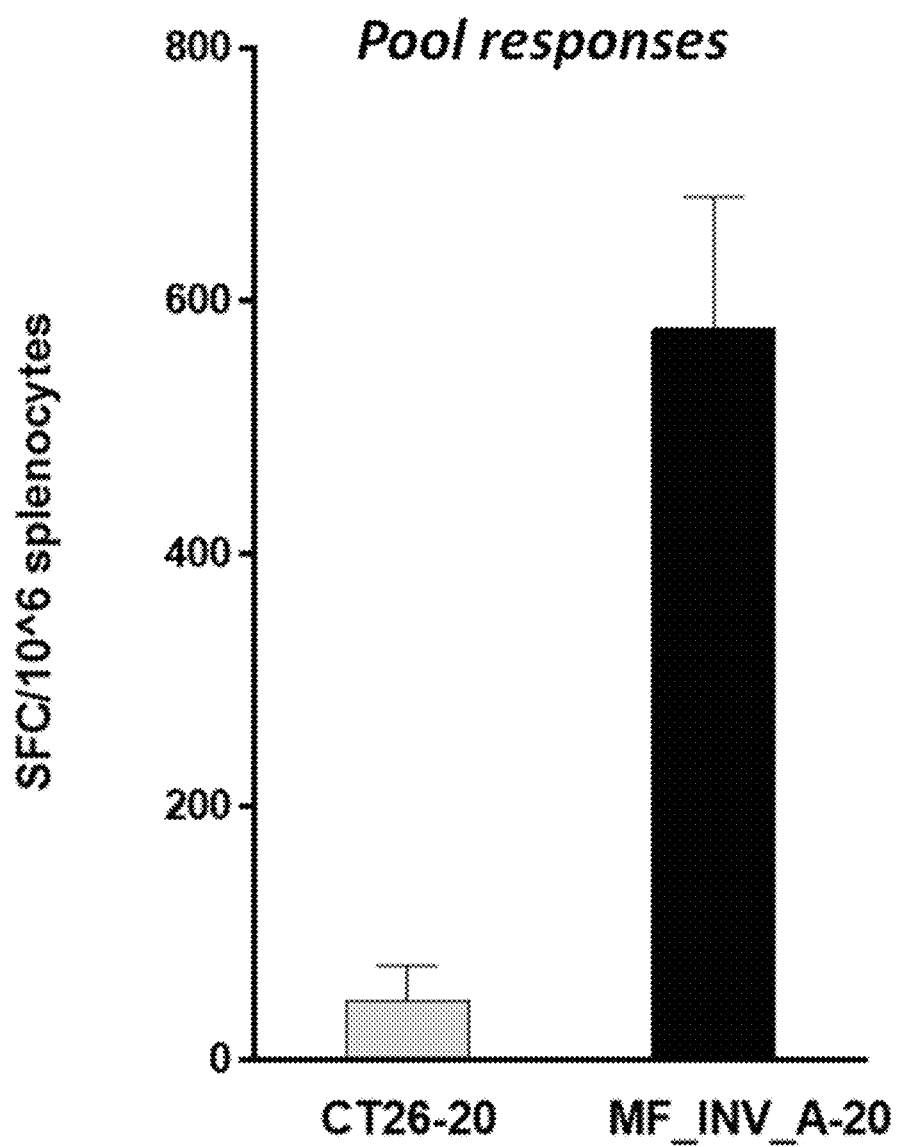

FIG. 3: Immunogenicity of GAd vectors encoding twenty CT26 neoantigens. Mice were immunized with $5\times10^7$ of each GAd vector: (1) MF_INV_A-20, which includes the MF Invariant chain FRAG A and the twenty CT26-20 neoantigens, or (2) CT26-20, which includes the twenty CT26 neoantigens but lacks an invariant chain fragment. After 2 weeks immune responses were measured by ELISpot assay on spleen cells. Shown are the responses (number of T cells producing IFNγ per millions of splenocytes) to a pool of 20 synthetic peptides corresponding to the sequences of the 20 encoded neoantigen sequences. Values shown are mean+/−SEM from measurements performed on 6 mice/group.

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Klbl, H. eds. (1995), Helvetica Chimica Acta, CH-4010 Basel, Switzerland) and as described in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", edited by Susan Budavari et al., CRC Press, 1996, and the United States Pharmacopeia-25/National Formulary-20, published by the United States Pharmcopeial Convention, Inc., Rockville Md., 2001.

Throughout this specification and the claims which follow, unless the context requires otherwise, the word "comprise", and variations such as "comprises" and "comprising", will be understood to imply the inclusion of a stated feature, integer or step or group of features, integers or steps but not the exclusion of any other feature, integer or step or group of integers or steps. In the following passages different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

Definitions

In the following, some definitions of terms frequently used in this specification are provided. These terms will, in each instance of its use, in the remainder of the specification have the respectively defined meaning and preferred meanings.

The term transmembrane domain (TMD) is used in the present invention to refer to the TMD of invariant chain sequences (INVs) is defined as the amino acid segment starting 17 residues N-terminal of the Gln (Q) residue conserved in all INVs and ending 8 residues C-terminally from the conserved Q thus including a total of 26 residues.

The term membrane proximal domain (MPD) is used in the present invention to refer to the segment of 27 residues immediately C-terminal of the TMD of INVs.

The term "adjuvant" is used in the present invention as substances that enhance the immune response to the antigen. In addition adjuvants have also evolved as substances that can help in stabilizing formulations of antigens. Adjuvants are added to vaccines to stimulate the immune system's response to the target antigen, but do not provide immunity themselves. Adjuvants are needed to improve routing and adaptive immune responses to antigens. Adjuvants apply their effects through different mechanisms. For example, by extending the presence of antigen in the blood or/and helping the antigen presenting cells absorb antigen, and/or activating macrophages and lymphocytes and/or supporting the production of cytokines. Some adjuvants, such as alum, function as delivery systems by generating depots that trap antigens at the injection site, providing a slow release that continues to stimulate the immune system. Among described types of adjuvants there are i) Inorganic compounds: alum, aluminum hydroxide, aluminum phosphate, calcium phosphate hydroxide ii) Mineral oil: paraffin oil iii) Bacterial products: killed *Bordetella pertussis* bacteria, *Mycobacterium bovis*, toxoids iv) Nonbacterial organics: squalene, v) Delivery systems: detergents (Quil A), vi, Plant saponins from Quillaja (See *Quillaia*), Soybean, *Polygala senega*, vii) Cytokines: IL-1, IL-2, IL-12, viii) Combination: Freund's complete adjuvant, Freund's incomplete adjuvant.

The term "immunomodulator" is used in the present invention to refer any drug or substance that has an effect on the immune system. An immunomodulator can adjust the immune response to the correct level by: i) strengthen weak immune systems ii) control overactive immune systems. A particular class of immunomodulators able to strengthen weak immune systems are modulators of immunological check point molecules (MCM) consisting of i) agonistic activator MCMs like a tumor necrosis factor (TNF) receptor superfamily member, preferably of CD27, CD40, OX40, GITR or CD137 ii) antagonistic inhibitory MCMs like PD-1, CD274, A2AR, B7-H3, B7-H4, BTLA, CTLA-4, IDO, KIR, LAG3, TIM-3, VISTA or B7-CD28 superfamily member, CD28 or ICOS or an antagonist of a ligand thereof.

Another class of immunomodulators that can strength a weak immune system are cytokines, which are acting as T cells growth factors. Preferred examples of such cytokines are IL-2, IL-12, IL-15, or IL-17.

The term "antigen" is used in the context of the present invention to refer to any structure recognized by molecules of the immune response, e.g. antibodies, T cell receptors (TCRs) and the like. Preferred antigens are cellular or foreign, e.g. viral bacterial or fungal) proteins that are associated with a particular disease. Antigens are recognized by highly variable antigen receptors (B-cell receptor or T-cell receptor) of the adaptive immune system and may elicit a humoral or cellular immune response. Antigens that elicit such a response are also referred to as immunogen. A fraction of the proteins inside cells, irrespective of whether they are foreign or cellular, are processed into smaller peptides and presented to by the major histocompatibility complex (MHC).

The term "antigenic fragment thereof" refers to a part of a given antigen that is still recognized by a molecule of the immune system. An antigenic fragment will comprise at least one epitope or antigenic determinant. Preferably, the antigenic fragments of the invention comprise at least one T cell epitope.

The term "epitope", also known as antigenic determinant, is used in the context of the present invention to refer to the segment of an antigen, preferably peptide that is bound by molecules of the immune system, e.g. B-cell receptors, T-cell receptors or antibodies. The epitopes bound by antibodies or B cells are referred to as "B cell epitopes" and the epitopes bound by T cells are referred to as "T cell epitopes". In this context, the term "binding" preferably relates to a specific binding, which is defined as a binding with an association constant between the antibody or T cell receptor (TCR) and the respective epitope of $1 \times 10^5$ M−1 or higher, preferably of $1 \times 10^6$ M−1, $1 \times 10^7$ M−1, $1 \times 10^8$ M−1 or higher. The skilled person is well aware how to determine the association constant (see e.g. Caoili, S. E. (2012) Advances in Bioinformatics Vol. 2012). Preferably, the specific binding of antibodies to an epitope is mediated by the Fab (fragment, antigen binding) region of the antibody, specific binding of a B-cell is mediated by the Fab region of the antibody comprised by the B-cell receptor and specific binding of a T-cell is mediated by the variable (V) region of the T-cell receptor. T cell epitopes are presented on the surface of an antigen presenting cell, where they are bound to Major Histocompatibility (MHC) molecules. There are at least two different classes of MHC molecules termed MHC class I, II respectively. Epitopes presented through the MHC-I pathway elicit a response by cytotoxic T lymphocytes (CD8+ cells), while epitopes presented through the MHC-II pathway elicit a response by T-helper cells (CD4+ cells). T cell epitopes presented by MHC Class I molecules are typically peptides between 8 and 11 amino acids in length and T cell epitopes presented by MHC Class II molecules are typically peptides between 13 and 17 amino acids in length. MHC Class III molecules also present non-peptidic epitopes as glycolipids. Accordingly, the term "T cell epitope" preferably refers to a 8 to 11 or 13 to 17 amino acid long peptide that can be presented by either a MHC Class I or MHC Class II molecule. Epitopes usually consist of chemically active surface groupings of amino acids, which may or may not carry sugar side chains and usually have specific three-dimensional structural characteristics, as well as specific charge characteristics. Conformational and non-conformational epitopes are distinguished in that the binding to the former but not the latter is lost in the presence of denaturing solvents.

The term "cancer specific antigen" is used in the context of the present invention to refer to a protein that is specifically expressed in cancer cells or is more abundant in cancer cells than in healthy cells. Cancer specific antigens include the following types of antigens:
  (i) oncofetal (typically only expressed in fetal tissues and in cancerous somatic cells); or
  (ii) oncoviral (encoded by tumorigenic transforming viruses); or
  (iii) overexpressed/accumulated (expressed by both normal and neoplastic tissue, with the level of expression highly elevated in neoplasia), e.g. tyrosinase in melanomas or Her-2 receptor in breast cancer; or
  (iv) cancer-testis (expressed only by cancer cells and adult reproductive tissues such as testis and placenta); or
  (v) lineage-restricted (expressed largely by a single cancer histotype); or
  (vi) cancer-specific isoform (alteration of the transcript exon composition).

The term "cancer specific neoantigen" is used in the context of the present invention to refer to an antigen not present in normal/germline cells but which occurs in transformed, in particular cancerous cells. A cancer specific neoantigen may comprise one or more, e.g. 2, 3, 4, 5 or more neoepitopes. It is preferred that the length of each cancer specific neoantigen included in the polypeptide of the present invention is selected in such to ascertain that they there is a low likelihood of comprising epitopes that occur in normal/germline cells. Typically, this can be ascertained in that the cancer specific neoantigen comprises 12 or less amino acids C-terminally and/or N-terminally of the amino acid change(s) that created the neoepitope.

The cancer specific neoantigen is preferably generated by a mutation occurring at level of DNA and wherein the mutated protein can comprise
  a) one or more single aa changes caused by a point mutation non-synonymous SNV; and/or
  b) a non-wildtype amino acid sequence caused by insertions/deletions resulting in frame shifted peptide; and/or
  c) a non-wildtype amino acid sequence caused by alteration of exon boundaries or by mutations generating intron retention; and/or
  d) a mutated cancer protein generated by a gene fusion event.

A neoantigen that is the result of one or more single amino acid changes caused by a genomic point mutation non-synonymous SNV is referred to in the context of the present invention as a single amino acid mutant peptide.

The term "frame-shift peptide" is used in the context of the present invention to refer to the complete non wild-type translation product of the protein-encoding segment of a polynucleotide comprising an insertion or deletion mutations causing a shift of the Open Reading Frame (ORF).

The term "open reading frame" abbreviated "ORF" is used in the context of the present invention to refer to a sequence of nucleotides that can be translated into a consecutive string of amino acids. Typically, an ORF contains a start codon, a subsequent region usually having a length which is a multiple of 3 nucleotides, but does not contain a stop codon (TAG, TAA, TGA, UAG, UAA, or UGA) in the given reading frame. An ORF codes for a protein where the amino acids into which it can be translated form a peptide-linked chain.

The term "polynucleotide" or "nucleic acid" includes both single-stranded and double-stranded nucleotide polymers. The nucleotides comprising the polynucleotide can be ribonucleotides or deoxyribonucleotides or a modified form of either type of nucleotide. Said modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phoshoranilladate and phosphoroamidate. Examples of polynucleotides are DNA and RNA.

An "isolated polynucleotide" is DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature.

The term "expression cassette" is used in the context of the present invention to refer to a polynucleotide which comprises at least one nucleic acid sequence that is to be expressed, e.g. a nucleic acid encoding a string of cancer specific neoantigens fused to invariant chain of the present invention or fragments thereof, operably linked to transcription and/or translation control sequences. Preferably, an expression cassette includes cis-regulating elements for efficient expression of a given gene, such as promoter, initiation-site and/or polyadenylation-site. Preferably, an expression cassette contains all the additional elements required for the expression of the polynucleotide in the cell of a patient. A typical expression cassette thus contains a promoter operatively linked to the polynucleotide sequence to be expressed and signals required for efficient polyadenylation of the transcript, ribosome binding sites, and translation termination. Additional elements of the cassette may include, for example enhancers. An expression cassette preferably also contains a transcription termination region downstream of the structural gene to provide for efficient termination. The termination region may be obtained from the same gene as the promoter sequence or may be obtained from a different gene.

The term "operably linked" as used in the context of the present invention refers to an arrangement of elements, wherein the components so described are configured so as to perform their usual function. A polynucleotide is "operably linked" when it is placed into a functional relationship with another nucleic acid sequence. For example, a promoter is operably linked to one or more transgenes, if it affects the transcription of the one or more transgenes. Further, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

The terms "vector" or "expression vector" are used interchangeably and refer to a polynucleotide, a polynucleotide within some type of envelope, e.g. a viral coat or a liposome, or a polynucleotide complexed with proteins capable of being introduced or of introducing the polynucleotide of the present invention or into a cell, preferably a mammalian cell.

Examples of vectors include but are not limited to plasmids, cosmids, phages, liposomes, viruses or artificial chromosomes. In particular, a vector is used to transport the promoter and the polynucleotide of the invention into a suitable host cell. Expression vectors may contain "replicon" polynucleotide sequences that facilitate the autonomous replication of the expression vector in a host cell. Once in the host cell, the expression vector may replicate independently of or coincidental with the host chromosomal DNA, and several copies of the vector and its inserted DNA can be generated. In case that replication incompetent expression vectors are used—which is often the case for safety reasons—the vector may not replicate but merely direct expression of the polynucleotide. Depending on the type of expression vector the expression vector may be lost from the cell, i.e. only transiently expresses the neoantigens encoded by the polynucleotide or may be stable in the cell. Expression vectors typically contain expression cassettes, i.e. the necessary elements that permit transcription of the polynucleotide into an mRNA molecule. If the polynucleotide is RNA transcription is not necessary and, thus the RNA molecules only require translation control elements The term "T cell enhancer amino acid sequence" refers to a polypeptide sequences that when fused to an antigenic sequence increases the induction of T cells in the context of a genetic vaccination.

The term "T cell response enhancer activity" refers to compounds, in particular polypeptides, which increase the response of T cells challenged with an antigen. An example of such a compound would be the polypeptide of the present invention in particular if coupled to an antigenic sequence. The polypeptide would increase the T cell response to said antigens compared to the T cell response to the antigen alone in the context of vaccination. Suitable assays to measure T cell response are known in the art and include the measurement of cytokines released by activated T cells such as interferon gamma (IFN-γ) by ELISpot or intracellular cytokine staining (ICS) which detects the production and accumulation of cytokines within the endoplasmic reticulum after cell stimulation. A compound with T cell response enhancer activity increases the response of the T cell as exemplified e.g. by an increase in cytokine release.

The terms "preparation" and "composition" as used in the context of the present invention are intended to include the formulation of the active compound, e.g. the Great Apes Adeno of the present invention with a carrier and/or excipient.

"Pharmaceutically acceptable" as used in the context of the present invention means approved by a regulatory agency of the Federal or a state government or listed in the U.S. Pharmacopeia or other generally recognized pharmacopeia for use in animals, and more particularly in humans.

The term "carrier", as used herein, refers to a pharmacologically inactive substance such as but not limited to a diluent, excipient, surfactants, stabilizers, physiological buffer solutions or vehicles with which the therapeutically active ingredient is administered. Such pharmaceutical carriers can be liquid or solid. Liquid carrier include but are not limited to sterile liquids, such as saline solutions in water and oils, including but not limited to those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. A saline solution is a preferred carrier when the pharmaceutical composition is administered intravenously. Examples of suitable pharmaceutical carriers are described in "Remington's Pharmaceutical Sciences" by E. W. Martin.

Suitable pharmaceutical "excipients" include starch, glucose, lactose, sucrose, gelatine, malt, rice, flour, chalk, silica gel, sodium stearate, glycerol monostearate, talc, sodium chloride, dried skim milk, glycerol, propylene, glycol, water, ethanol and the like.

"Surfactants" include anionic, cationic, and non-ionic surfactants such as but not limited to sodium deoxycholate, sodium dodecylsulfate, Triton X-100, and polysorbates such as polysorbate 20, polysorbate 40, polysorbate 60, polysorbate 65 and polysorbate 80.

"Stabilizers" include but are not limited to mannitol, sucrose, trehalose, albumin, as well as protease and/or nuclease antagonists.

"Physiological buffer solution" that may be used in the context of the present invention include but are not limited to sodium chloride solution, demineralized water, as well as suitable organic or inorganic buffer solutions such as but not limited to phosphate buffer, citrate buffer, tris buffer (tris (hydroxymethyl)aminomethane), HEPES buffer ([4 (2 hydroxyethyl)piperazino]ethanesulphonic acid) or MOPS buffer (3 morpholino-1 propanesulphonic acid). The choice of the respective buffer in general depends on the desired buffer molarity. Phosphate buffer are suitable, for example, for injection and infusion solutions.

An "effective amount" or "therapeutically effective amount" is an amount of a therapeutic agent sufficient to achieve the intended purpose. The effective amount of a given therapeutic agent will vary with factors such as the nature of the agent, the route of administration, the size and species of the animal to receive the therapeutic agent, and the purpose of the administration. The effective amount in each individual case may be determined empirically by a skilled artisan according to established methods in the art.

As used herein, "treat", "treating", "treatment" or "therapy" of a disease or disorder means accomplishing one or more of the following: (a) reducing the severity of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in an individual that has previously had the disorder(s); and (e) limiting or preventing recurrence of symptoms in individuals that were previously symptomatic for the disorder(s).

Embodiments of the Invention

In a first aspect the present invention provides a polypeptide comprising:
(a) a fragment of an INV of a Teleostei, which preferably has T cell response enhancer activity, comprising or consisting of between 16 to 27 contiguous amino acids of the membrane proximal domain (MPD) of an INV of the Teleostei, wherein the MPD is preferably characterized by the following amino acid sequence (SEQ ID NO: 31):

$X_1QKX_2QIHTLQKX_3SX_4RX_5X_6X_7QX_8TRX_9SX_{10}AV$ wherein
$X_1$ is G, D, S or N, preferably G or S; and more preferably G;
$X_2$ is E or Q; preferably E;
$X_3$ is N or S; preferably N;
$X_4$ is D or E; preferably E;

$X_5$ is M or L; preferably M;
$X_6$ is G, N, S or T; preferably S, G or T, and more preferably S;
$X_7$ is K or R; preferably K;
$X_8$ is L or M; preferably L;
$X_9$ is S, T or A; preferably S; and
$X_{10}$ is Q or H; preferably Q;
and wherein the 16 to 27 amino acids of the MPD are preferably at least 70% identical to SEQ ID NO: 7;
and optionally one or more antigens or antigenic fragments thereof;
or
(b) a full length Teleostei INV of SEQ ID NO: 1 or a variant thereof, which has T cell response enhancer activity, wherein the amino acid sequence of the MPD of the variant is at least 80% identical to SEQ ID NO: 7;
And one or more antigens or antigenic fragments thereof.

Generally it is desired that the fragment of an INV is as short as possible while retaining its T cell antigen stimulatory effect. Preferably, the fragment comprises, more preferably consists of 16 to 27, 17 to 26, 18 to 25, 19 to 24, 20 to 23, 21 to 22 continuous amino acids of the MPD of an INV.

While the fragment of the INV can comprise additional sequences N- and/or C-terminally of the MPD, it is preferred that no such sequences are comprised in the fragment and, thus, it is preferred that the fragment consists of the respective continuous stretch of amino acids of the MPD.

If the fragment of the INV comprises additional sequences N- and/or C-terminally of the MPD, it is preferred that the fragment comprises the entire MPD, i.e. 27 amino acids. It is preferred that the fragment does not comprise the TMD but comprises additional C-terminal amino acids of the INV. Preferably, these C-terminal amino acids are immediately consecutive to the MPD.

The sequence of the MPD is preferably based on the MPD sequence of Mandarin fish according to SEQ ID NO: 7. Preferably, the fragment comprises or consists of 16 to 27 amino acids of the MPD, wherein the MPD is at least 75%, more preferably at least 80%, more preferably at least 85%, more preferably at least 90%, more preferably at least 95% identical to SEQ ID NO: 7.

The fragment may comprise additional N- and/or C-terminal amino acid sequences of an INV. Thus, it preferred that the overall length of the fragment of the INV is between 16 to 80, 17 to 72, 18 to 55, 19 to 50, 20 to 45, 21, to 40, 22 to 35, 23 to 30 contiguous amino acids.

In a preferred embodiment the fragment comprises or consist of the MPD characterized by the amino acid sequence of SEQ ID NO: 31. Preferably, this MPD comprises at least the amino acid sequence of QIHTLQKX$_3$SX$_4$RX$_5$X$_6$X$_7$QX$_8$ (SEQ ID NO: 51), wherein
$X_3$ is N or S; preferably N;
$X_4$ is D or E; preferably E;
$X_5$ is M or L; preferably M;
$X_6$ is G, N, S or T; preferably S, G or T, and more preferably S;
$X_7$ is K or R; preferably K;
$X_8$ is L or M; preferably L.

In the context of this preferred embodiment it is particularly preferred that this fragment comprises SEQ ID NO: 51 and between 0 to 11, i.e. 0, 1, 2, 3, 4, 5, 6, 7, 8, 9, 10 or 11 additional amino acids of a MPD, which may be present N- and/or C-terminally of SEQ ID NO: 51. Preferably these 1 to 11 further amino acids share at least 70% identity with SEQ ID NO: 7. Preferably, the entire fragment including the core sequence according to SEQ ID NO: 51 is at least 70% identical to SEQ ID NO: 7, more preferably at least 75%, more preferably at least 80%, even more preferably at least 85% or at least 90% identical to SEQ ID NO: 7. In each case it is preferred that the fragment has T cell response enhancer activity. It is further preferred that there are no further INV chain sequences continuous to the N- and C-terminus of the fragment and more preferably that the fragment is the sole INV sequence in the polypeptide.

In a preferred embodiment of the polypeptide of the first aspect of the invention the amino acid sequence:
(a) of the MPD of alternative (a) of the first aspect is any of SEQ ID NOs: 7 to 12, i.e. 7, 8, 9, 10, 11 or 12; or
(b) of the INV fragment of alternative (a) of the first aspect of the invention comprises any of SEQ ID NOs: 7, 8, 9, 10, 11, 12, 13, 14, 15, 16, 17 or 18, preferably of 7 or 13; or consists any of any of SEQ ID NOs: 7, 8, 9, 10, 11, 12, 13, 14, 15, 16, 17 or 18, preferably of 7 or 13; or
(c) of the Teleostei invariant chain of alternative (b) of the first aspect of the invention is any of SEQ ID NOs: 1 to 6.

If the fragment consists of 16 to 27 amino acids of the MPD of an INV, preferred fragments have a length of 16 to 27, 17 to 26, 18 to 25, 19 to 24, 20 to 23, 21 to 22 continuous amino acids of the MPD of the INV according to SEQ ID NO: 7 to 12.

In each case outlined above the fragment or variant has T cell response enhancer activity. T cell response enhancer activity can be measured as known in the art or as set out in the attached experiments. It is preferred that the T cell response enhancer activity is at least 50%, preferably at least 80% of the T cell response enhancer activity of the INV fragment according to SEQ ID NO: 13, when coupled to the same antigen or string of antigens.

In a particular embodiment of the polypeptide of alternative (a) of the first aspect of the invention the fragment consists of at least 16 to 27 N-terminal amino acids of the MPD and:
(i) 1 to 26 consecutive amino acids of the transmembrane domain (TMD) of an INV of a Teleostei immediately N-terminal of the MPD, wherein the TMD of the INV of the Teleostei is preferably characterized by the following amino acid sequence (SEQ ID NO: 32):
AY$_1$KY$_2$AY$_3$LTTLY$_4$CLLY$_5$Y$_6$SQVFTAYY$_7$VF
wherein
$Y_1$ is L or F, preferably L;
$Y_2$ is I or V, preferably V;
$Y_3$ is G or A, preferably G;
$Y_4$ is T or A, preferably T;
$Y_5$ is L or V, preferably L;
$Y_6$ is A or S, preferably A; and
$Y_7$ is M or T, preferably M;
and/or
(ii) 1 to 19 consecutive amino acids of the INV of a Teleostei immediately C-terminal of the MPD preferably characterized by the following amino acid sequence (SEQ ID NO: 33):
APZ$_1$Z$_2$MZ$_3$Z$_4$PMZ$_5$SLPZ$_6$Z$_7$Z$_8$DZ$_9$Z$_{10}$
wherein
$Z_1$ is M, V or A, preferably M or V, more preferably M;
$Z_2$ is R or K, preferably K;
$Z_3$ is H, A or Q, preferably M or H, more preferably H;
$Z_4$ is M or L, preferably M;
$Z_5$ is N or S, preferably N;
$Z_6$ is M or L, preferably L;
$Z_7$ is M, L or V, preferably L;

$Z_8$ is M or S, preferably M;
$Z_9$ is F or Y, preferably F; and
$Z_{10}$ is T or S, preferably T.

If the fragment comprises additional N- and/or C-terminal amino acid sequences of an INV, it is preferred that the overall length of the fragment of the INV is between 28 to 72, 30 to 65, or 35 to 46 contiguous amino acids.

It has been surprisingly found by the present inventors that a strong T cell response to two or more antigens, preferably neoantigens can be induced by fusing the INV fragment of alternative (a) of the first aspect of the invention or the INV of alternative (b) of the first aspect of the invention to two or more antigens and/or antigenic fragments thereof. This allows the simultaneous induction of a T cell response against multiple antigens. Thus, regarding both alternative (a) of the first aspect of the invention and alternative (b) of the first aspect of the invention it is preferred that the polypeptide comprises multiple antigens and/or or antigenic fragments thereof. For example, it is preferred that the polypeptide comprises at least 5 different antigens and/or or antigenic fragments thereof, more preferably at least 20 different antigens and/or or antigenic fragments thereof, even more preferably at least 50 different antigens and/or or antigenic fragments thereof, even more preferably at least 100 different antigens and/or or antigenic fragments thereof, even more preferably at least 200 different antigens and/or or antigenic fragments thereof and even more preferably at least 300 different antigens and/or or antigenic fragments thereof.

To accommodate the maximum number of different antigens within one polypeptide it is particularly preferred that the polypeptide comprises antigenic fragments of the antigens.

The antigens are chosen depending on the respective therapeutic application. If the therapeutic or prophylactic vaccination against a proliferative disease is desired the antigen is selected from a cancer-specific antigen or a cancer specific neoantigen. As set out above in particular in the context of cancer vaccination it is preferred that the polypeptide of the first aspect comprises two or more different antigens. It is preferred that the polypeptide comprises at least 5 different cancer specific antigens or antigenic fragments thereof, more preferably at least 20 different cancer specific antigens or antigenic fragments thereof, even more preferably at least 50 different cancer specific antigens or antigenic fragments thereof, even more preferably at least 100 different cancer specific antigens or antigenic fragments thereof, even more preferably at least 200 different cancer specific antigens or antigenic fragments thereof and even more preferably at least 300 different cancer specific antigens or antigenic fragments thereof. Alternatively, it is preferred that the polypeptide comprises at least 5 different cancer specific neoantigens or antigenic fragments thereof, more preferably at least 20 different cancer specific neoantigens or antigenic fragments thereof, even more preferably at least 50 different cancer specific neoantigens or antigenic fragments thereof, even more preferably at least 100 different cancer specific neoantigens or antigenic fragments thereof, even more preferably at least 200 different cancer specific neoantigens or antigenic fragments thereof and even more preferably at least 300 different cancer specific neoantigens or antigenic fragments thereof. Alternatively, it is preferred that the polypeptide comprises at least 5 different cancer specific antigens or neoantigens or antigenic fragments thereof, more preferably at least 20 different cancer specific antigens or neoantigens or antigenic fragments thereof, even more preferably at least 50 different cancer specific antigens or neoantigens or antigenic fragments thereof, even more preferably at least 100 different cancer specific antigens or neoantigens or antigenic fragments thereof, even more preferably at least 200 different cancer specific antigens or neoantigens or antigenic fragments thereof and even more preferably at least 300 different cancer specific antigens or neoantigens or antigenic fragments thereof.

Alternatively, the antigen is a viral protein or an antigenic fragment thereof, a bacterial protein or an antigenic fragment thereof or a fungal protein or an antigenic fragment thereof.

Generally, the prophylactic or therapeutic vaccination against viral, bacterial or fungal infection does not require as many different antigens to be effective as the vaccination in the therapy of proliferative diseases. Nevertheless, there are some viruses like, e.g. HIV that have a large epitope diversity, in particular in the coat proteins. To elicit a broad immune response multiple antigens can be included. It is, thus preferred that the polypeptide comprises at least 5 different viral antigens or an antigenic fragment thereof, more preferably at least 20 different viral antigens or an antigenic fragment thereof, even more preferably at least 50 different viral antigens or an antigenic fragment thereof, even more preferably at least 100 different viral antigens or an antigenic fragment thereof, even more preferably at least 200 different viral antigens or an antigenic fragment thereof and even more preferably at least 300 different viral antigens or an antigenic fragment thereof. The antigens may be chosen from different strains of the same virus and/or from different viral species. In the latter case the vaccine allows immunization against a variety of different viral species.

Alternatively, it is preferred that the polypeptide comprises at least 5 different bacterial antigens or an antigenic fragment thereof, more preferably at least 20 different bacterial antigens or an antigenic fragment thereof, even more preferably at least 50 different bacterial antigens or an antigenic fragment thereof, even more preferably at least 100 different bacterial antigens or an antigenic fragment thereof, even more preferably at least 200 different bacterial antigens or an antigenic fragment thereof and even more preferably at least 300 different bacterial antigens or an antigenic fragment thereof.

Alternatively, it is preferred that the polypeptide comprises at least 5 different fungal antigens or an antigenic fragment thereof, more preferably at least 20 different fungal antigens or an antigenic fragment thereof, even more preferably at least 50 different fungal antigens or an antigenic fragment thereof, even more preferably at least 100 different fungal antigens or an antigenic fragment thereof, even more preferably at least 200 different fungal antigens or an antigenic fragment thereof and even more preferably at least 300 different fungal antigens or an antigenic fragment thereof.

In all of above embodiments it is preferred that the antigens are T cell antigens. T cell antigens are those that are presented by MHC and elicit a T cell response.

Preferably, the antigen or each of the antigens or an antigenic fragments thereof has(have) a length between 6 to 100 amino acids, more preferably 7 to 50 and more preferably 8 to 30 amino acids.

In a preferred embodiment of the polypeptide of the first aspect of the invention the one or more antigens and/or one or more antigenic fragments thereof are located C-terminally of the fragment of the INV according to alternative (a) of the first aspect of the invention or the full length INV according to alternative (b) of the first aspect of the invention. It is particularly preferred that the antigens and/or antigenic fragments thereof are immediately C-terminally to the INV according to alternative (a) or (b) of the first aspect of the invention.

It is preferred that the polypeptides of the invention are produced inside cells of the patient to be vaccinated. The intracellular expression is a prerequisite for MHC presentation and, thus stimulation of a T cell response. Accordingly, in a second aspect the present invention relates to a polynucleotide encoding the polypeptide according to the first aspect of the present invention. Preferably, the polynucleotide is a DNA or RNA. More preferably the polynucleotide is DNA. RNA is preferably used to directly elicit translation of the encoded polypeptide. DNA encoding the polypeptide of the first aspect is typically inserted into expression cassettes, which direct transcription of mRNA encoding the polypeptides of the invention. However, the polynucleotide may also be RNA if the polynucleotide is comprised in a vector and the vector is a RNA virus. A preferred RNA for direct application is a self-amplifying RNA (SAM).

In a third aspect the present invention relates to a vector comprising the polynucleotide according to the second aspect of the invention. Preferably the polynucleotide of the present invention is operably linked to an expression control sequence.

Two or more vectors are used, if the number of different antigens or antigenic fragments thereof to be delivered to a patient is so large that a polynucleotide encoding the fusion polypeptide of the INV and all antigens or antigenic fragments thereof cannot be accommodated in the chosen vector. Accordingly, in a fourth aspect the present invention relates to a collection of two or more different vectors, wherein the different vectors each comprise a polynucleotide according to the second aspect of the present invention encoding a different polypeptide according to the first aspect of the present invention.

The vector of the third aspect or the collection of vectors of the fourth aspect, wherein the vector in each case is independently selected from the group consisting of a plasmid; a cosmid; a liposomal particle, a viral vector or a virus like particle; preferably an alphavirus vector, a venezuelan equine encephalitis (VEE) virus vector, a sindbis (SIN) virus vector, a semliki forest virus (SFV) virus vector, a simian or human cytomegalovirus (CMV) vector, a Lymphocyte choriomeningitis virus (LCMV) vector, a retroviral vector, a lentiviral vector, an adenoviral vector, an adeno-associated virus vector a poxvirus vector, a vaccinia virus vector or a modified vaccinia ankara (MVA) vector. It is preferred that a collection of vectors, wherein each member of the collection comprises a polynucleotide encoding a different antigen or fragments thereof and, which is thus typically administered simultaneously uses the same vector type, e.g. an adenoviral derived vector.

The most preferred vectors are adenoviral vectors, in particular adenoviral vectors derived from human or non-human great apes. Preferred great apes from which the adenoviruses are derived are Chimpanzee (*Pan*), Gorilla (*Gorilla*) and orangutans (*Pongo*), preferably Bonobo (*Pan paniscus*) and common Chimpanzee (*Pan troglodytes*). Typically, naturally occurring non-human great ape adenoviruses are isolated from stool samples of the respective great ape. The most preferred vectors are non-replicating adenoviral vectors based on hAd5, hAd11, hAd26, hAd35, hAd49, ChAd3, ChAd4, ChAd5, ChAd6, ChAd7, ChAd8, ChAd9, ChAd10, ChAd11, ChAd16, ChAd17, ChAd19, ChAd20, ChAd22, ChAd24, ChAd26, ChAd30, ChAd31, ChAd37, ChAd38, ChAd44, ChAd55, ChAd63, ChAd 73, ChAd82, ChAd83, ChAd146, ChAd147, PanAd1, PanAd2, and PanAd3 vectors or replication-competent Ad4 and Ad7 vectors. The human adenoviruses hAd4, hAd5, hAd7, hAd11, hAd26, hAd35 and hAd49 are well known in the art. Vectors based on naturally occurring ChAd3, ChAd4, ChAd5, ChAd6, ChAd7, ChAd8, ChAd9, ChAd10, ChAd11, ChAd16, ChAd17, ChAd19, ChAd20, ChAd22, ChAd24, ChAd26, ChAd30, ChAd31, ChAd37, ChAd38, ChAd44, ChAd63 and ChAd82 are described in detail in WO 2005/071093. Vectors based on naturally occurring PanAd1, PanAd2, PanAd3, ChAd55, ChAd73, ChAd83, ChAd146, and ChAd147 are described in detail in WO 2010/086189.

In a fifth aspect the present invention relates to a pharmaceutical composition comprising the polypeptide of the first aspect of the present invention, a polynucleotide of the second aspect of the present invention or a vector of the third aspect of the present invention or collection of vectors of the fourth aspect of the invention and a pharmaceutically acceptable excipient and optionally one or more adjuvants.

The present inventors have found that the administration of at least one immunomodulator, for example a modulator of a checkpoint molecule (MCM), further improves the strength of the T cell response to the antigen or a fragment thereof. Thus, in a preferred embodiment of the sixth aspect the pharmaceutical composition comprises at least one immunomodulator, for example a MCM, or at least one polynucleotide encoding the immunomodulator, for example a MCM, or a vector or liposomal particle comprising the polynucleotide encoding the immunomodulator, for example a MCM.

In a sixth aspect the present invention relates to a kit of parts comprising the pharmaceutical composition of the fifth aspect of the present invention and separately packaged at least one immunomodulator, for example a MCM, or at least one polynucleotide encoding the immunomodulator, for example a MCM, or a vector comprising the polynucleotide encoding the the immunomodulator, for example a MCM.

In a preferred embodiment of the fifth aspect or sixth aspect the immunomodulator is a MCM and is selected from the group consisting of:
  (a) an agonist of a tumor necrosis factor (TNF) receptor superfamily member, preferably of CD27 (e.g. Varlilumab), CD40 (e.g. CP-870,893), OX40 (e.g. INCAGN01949 or MEDI0562), GITR (e.g. MEDI1873) or CD137 (e.g. Utomilumab);
  (b) an antagonist of PD-1 (e.g. pembrolizumab or nivolumab), CD274 (atezolizumab or Durvalumab), A2AR (e.g. Preladenant), B7-H3 (e.g. MGA271), B7-H4, BTLA, CTLA-4 (e.g. Tremelimumab or AGEN1884), IDO, KIR, LAG3, TIM-3 (e.g. CA-327 or RMT3-23), or VISTA (e.g. CA-170) or an antagonist of a B7-CD28 superfamily member, preferably of CD28 or ICOS or an antagonist of a ligand thereof.
Other preferred immunomodulators are cytokines that act as T cell growth factors, in particular IL-2, IL-12, or IL-15.

In a seventh aspect the present invention relates to a polypeptide according to the first aspect of the invention, a polynucleotide according to the second aspect of the invention, or a vector or a collection of vectors according to third or fourth aspect of the invention for use as a medicament.

In an eight aspect the present invention relates to polypeptide according to the first aspect of the invention, a polynucleotide according to the second aspect of the invention, or a vector or a collection of vectors according to third or fourth aspect of the invention, or a pharmaceutical composition according to the fifth aspect of the invention or kits comprising such pharmaceutical compositions according to the sixth aspect of the invention or use in preventing or treating a proliferative disease, preferably cancer, viral disease, fungal disease or bacterial disease.

In a preferred embodiment the polypeptide according to the first aspect of the invention, the polynucleotide according to the second aspect of the invention, or the vector or a collection of vectors according to third or fourth aspect of the invention, or the pharmaceutical composition or kits comprising such pharmaceutical compositions according fifth aspect of the invention, wherein the cancer is selected from the group consisting of malignant neoplasms of lip, oral cavity, pharynx, a digestive organ, respiratory organ, intrathoracic organ, bone, articular cartilage, skin, mesothelial tissue, soft tissue, breast, female genital organs, male genital organs, urinary tract, brain and other parts of central nervous system, thyroid gland, endocrine glands, lymphoid tissue, and haematopoietic tissue.

In a preferred embodiment the polypeptide according to the first aspect of the invention, the polynucleotide according to the second aspect of the invention, or the vector or a collection of vectors according to third or fourth aspect of the invention, or the pharmaceutical composition or kits comprising such pharmaceutical compositions according fifth aspect of the invention, wherein at least one immunomodulator, for example a MCM, or at least one polynucleotide encoding the immunomodulator, for example a MCM, or a vector or liposomal particle comprising the polynucleotide encoding the immunomodulator, for example a MCM, is administered prior to, concomitantly with or subsequently to the administration of the polypeptide according to the first aspect of the invention, the polynucleotide according to the second aspect of the invention, or the vector or a collection of vectors according to third or fourth aspect of the invention, or the pharmaceutical composition or kits comprising such pharmaceutical compositions according fifth aspect of the invention.

In a preferred embodiment of the eight aspect of the invention the administration of the modulator of a checkpoint molecule is initiated before initiation of administration of the vaccine, or wherein administration of the checkpoint inhibitor is initiated after initiation of administration of the vaccine, or wherein administration of the checkpoint inhibitor is initiated simultaneously with the initiation of administration of the vaccine.

In a preferred embodiment of the eight aspect of the invention the vaccination regimen is a heterologous prime boost with two different viral vectors. Preferred combinations are Great Apes derived adenoviral vector for priming and a poxvirus vector, a vaccinia virus vector or a modified vaccinia ankara (MVA) vector for boosting being. Preferably these are administered sequentially with an interval of at least 1 week, preferably of 6 weeks.

EXAMPLES

Example 1: Fusion of Neoantigens to Mandarin Fish Invariant Chain or Fragments Thereof Generates Immunogenicity in the Context of Great Apes Adenovirus Vaccination The selected cancer specific neoantigens are generated by 5 non-synonymous single-nucleotide variants (SNVs), the most frequent type of mutations found in tumors. The amino acid sequence of each cancer specific neoantigen has the mutated amino acid placed in its center flanked both upstream and downstream by 12 wild-type (wt) amino acids for a total length of 25aa (Table 1). Neoantigen sequences are joined head to tail to form the artificial antigen.

A Great Ape Adenoviral vector (GAd) encoding a pentatope containing 5 cancer specific neoantigens (Table 1) preceded by an initiator methionine (Penta: SEQ ID NO: 25) derived from the CT26 murine tumor is unable to induce an immune response against cancer specific neoantigens (FIG. 1) unless a Mandarin Fish invariant chain (INV) sequence (MF_INV_FL: SEQ ID NO: 26) or a truncated version of the Mandarin Fish INV comprising residues 1 to 81 which includes the transmembrane domain (MF_INV_SH, SEQ ID NO:27) or a fragment of the Mandarin fish INV sequence preceded by an initiator methionine (MF_INV_A: SEQ ID NO: 28; MF_INV_B: SEQ ID NO: 29) is placed at the N-terminus of the pentatope. In all constructs a HA peptide sequence (SEQ ID NO: 30) for the purpose of monitoring expression is fused downstream the pentatope.

The immunological potency was evaluated in BalBC inbred mice after single intramuscular immunization at a dose of $5 \times 10^8$ or $5 \times 10^7$ GAd viral particles (vp) for each of the vaccine constructs. Splenocytes were collected three weeks post-immunization and tested by IFN-γ ELISpot by stimulating cells in the presence of the pool of synthetic 25mer peptides corresponding to each of the 5 cancer specific neoantigens. IFN-γ ELISpot assays were performed on single-cell suspensions of spleens. MSIP 54510 plates (Millipore, Billerica, MA) were coated with 10 μg/ml of anti-mouse IFN-γ antibody (U-CyTech Utrecht, The Netherlands) and incubated overnight at 4° C. After washing and blocking, mouse splenocytes were plated in duplicate at two different densities ($1 \times 10^6$ and $5 \times 10^5$ cells per well) and stimulated overnight with a peptide pool comprising the five 25mer peptides at a final concentration of 1 μg/ml. The peptide diluent dimethyl sulfoxide (Sigma-Aldrich, Milan, Italy) was used as negative control. Plates were developed by subsequent incubations with biotinylated anti-mouse IFN-γ antibody (U-CyTech Utrecht, The Netherlands), conjugated streptavidin-alkaline phosphatase (BD Biosciences, San Jose, CA) and finally with 5-bromo-4-chloro-3-indoyl-phosphate/nitro blue tetrazolium 1-Step solution (Thermo Fisher Scientific, Rockford, IL). An automated ELISA-spot assay video analysis system automated plate reader was used to analyze plates. ELISpot data were expressed as IFN-γ SFCs per million splenocytes.

Immune responses (number of T cells producing IFN-γ per million splenocytes) are shown in FIG. 1. Responses were considered positive if (i) the mean of antigen wells was greater than 20 Spot Forming Colonies SFC/$10^6$ PBMC and (ii) exceeded by 3-fold the background value of wells incubated with the peptides diluent DMSO. As shown in FIG. 1, the addition of either Mandarin Fish INV or a fragment thereof converted the non-immunogenic Penta antigen into an immunogenic antigen with 100% response rate in animals vaccinated with MF_INV_FL or MF_INV_A in animals vaccinated at a dose of $5 \times 10^8$ vp. In particular vaccination at $5 \times 10^8$ vp with the constructs containing the short fragments MF_INV_A or MF_INV_B induced immunogenicity at levels comparable to that observed for the constructs containing either the full-length Mandarin Fish INV (MF_INV_FL) or a truncated version of the Mandarin Fish INV comprising residues 1 to 81 which includes the transmembrane domain (MF_INV_SH). Vaccination at $5 \times 10^7$ vp (FIG. 1) could discriminate the potency of the different T cell enhancer with the constructs containing the short fragments MF_INV_A being the only one able to rescue immunogenicity in 100% of mice at levels comparable to that observed for the constructs containing the full-length Mandarin Fish INV (MF_INV_FL).

The truncated version of the Mandarin Fish INV comprising residues 1 to 81 which includes the transmembrane domain (MF_INV_SH) is instead inferior to the MF_INV_A and being able to induce an immune response at the lower dosage only in 1 out of 6 mice.

TABLE 1

Penta antigen: Composition of the penta antigen. CT26 neoantigens are present in the assembled Penta antigen in the order shown. The mutated amino acid is indicated in bold and underlined for each neoantigen.

| SEQ ID NO | Neoantigen | Gene |
|---|---|---|
| 20 | LLPFYPPDEALEIGLELNSSALPPT | SLC4A3 |
| 21 | ILPQAPSGPSYATYLQPAQAQMLTP | E2F8 |
| 22 | KPLRRNNSYTSYIMAICGMPLDSFR | SLC20A1 |
| 23 | VIQTSKYYMRDVIAIESAWLLELAP | DHX35 |
| 24 | HIHRAGGLFVADAIQVGFGRIGKHF | AGXT2L2 |

Example 2

The capacity of the Mandarin Fish Invariant chain fragment MF_INV_A (SEQ ID NO: 7) to potentiate the vaccine-induced immune response was then further tested using a new artificial antigen containing a larger number (20) of neoantigens from the CT26 murine model. All five neoantigens present in construct MF_INV_A from example 1 (Table 1) where included in the new antigen but in a different order as compared to MF_INV_A (Table 2). Two GAd vectors each encoding the same 20 neoantigens joined head to tail in the order given by Table 2 were generated: construct CT26-20 with only an initiator methionine preceding the antigen (SEQ ID NO: 49) and construct MF_INV_A-20 where the Mandarin Fish Invariant chain FRAG A (SEQ ID NO: 7) preceded by an initiator methionine is placed at the N-terminus of the antigen (SEQ ID NO: 50). In both constructs a HA peptide sequence (SEQ ID NO: 30) is fused downstream of the antigen for the purpose of monitoring expression.

Immune responses were evaluated in vivo in BalBC inbred mice (n=6 per group) after a single intramuscular immunization at a dose of $5 \times 10^7$ viral particles (vp). Splenocytes were collected two weeks after immunization and tested by IFNγ ELISpot stimulating the cells in presence of a pool of 20 synthetic peptides corresponding to the sequences of the encoded neoantigens. As observed before for the small pentatope antigen the presence of MF invariant chain FRAG A (SEQ ID NO: 7) strongly enhanced the T cell responses post vaccination (FIG. 3), independently from the order and the total number of encoded neoantigens.

TABLE 2

Antigen composition of constructs CT26-20 and MF_INV_A-20: Identity of the 20 CT26 neoantigens present in the assembled CT26-20 and MF_INV_A-20 antigens. Neoantigens are present in the antigen in the order shown. The mutated amino acid is indicated in bold and underlined for each neoantigen. SEQ ID NOs: 20 to 24 correspond to the five neoantigens present in the pentatope (see Table 1).

| SEQ ID NO | Neoantigen |
|---|---|
| 34 | LRTAAYVNAIEKIFKVYNEAGVTFT |
| 35 | SNFTVDCSKAGNDMLLVGVHGPRTP |
| 21 | ILPQAPSGPSYATYLQPAQAQMLTP |
| 36 | ESDRNKESSDQTSVNMNGLENKISY |
| 20 | LLPFYPPDEALEIGLELNSSALPPT |
| 37 | QTSPTGILPTTSNSISTSEMTWKSS |
| 38 | AVQKLNLQNLVILQAPENLTLSNLS |
| 39 | TSIPSVSNALNWKEFSFIQSTLGYV |
| 40 | IIQVSPKDIQLTIFPSKSVKEGDTV |
| 24 | HIHRAGGLFVADAIQVGFGRIGKHF |
| 41 | HSGQNHLKEMAISVLEARACAAAGQ |
| 23 | VIQTSKYYMRDVIAIESAWLLELAP |
| 42 | KASKKGMWSEGNSSHTIRDLKYTIE |
| 43 | LPGFKGVKGHSGIDGLKGQPGAQGV |
| 44 | ALGSLALMIWLMTTPHSHETEQKRL |
| 45 | SWIHCWKYLSVQSQLFRGSSLLFRR |
| 22 | KPLRRNNSYTSYIMAICGMPLDSFR |
| 46 | EVATRMQSFGMKIVGYDPIISPEVA |
| 47 | TVSVVALHDDMENQPLIGIQSTAIP |
| 48 | FPEFARYTTPEDTTPEPGEDPRVTR |

The invention claimed is:

1. A polynucleotide comprising a sequence encoding a fusion polypeptide, wherein the fusion polypeptide having T-cell response enhancer activity comprises (a) a fragment of an invariant chain (INV) of a Teleostei comprising between 16 to 27 amino acids of the membrane proximal domain (MPD) of an INV of the Teleostei, wherein the MPD is characterized by the following amino acid sequence (SEQ ID NO: 31):

$X_1QKX_2QIHTLQKX_3SX_4RX_5X_6X_7QX_8TRX_9SX_{10}AV$ wherein $X_1$ is G, D, S or N; $X_2$ is E or Q; $X_3$ is N or S; $X_4$ is D or E; $X_5$ is M or L; $X_6$ is G, N, S or T; $X_7$ is K or R; $X_8$ is L or M; $X_9$ is S, T or A; and $X_{10}$ is Q or H; and wherein the 16 to 27 amino acids of the MPD are at least 90% identical to SEQ ID NO: 7;

and further comprises (b) one or more antigens and/or one or more antigenic fragments thereof;

wherein the fusion polypeptide does not comprise the full length INV of a Teleostei.

2. An expression vector comprising the polynucleotide according to claim 1, wherein the expression vector is selected from the group consisting of a plasmid; a cosmid; a liposomal particle, a viral vector or a virus like particle.

3. The expression vector of claim 2, wherein the expression vector is selected from the group consisting of: an alphavirus vector, a venezuelan equine encephalitis (VEE) virus vector, a sindbis (SIN) virus vector, a semliki forest virus (SFV) virus vector, a simian or human cytomegalovirus (CMV) vector, a Lymphocyte choriomeningitis virus (LCMV) vector, a retroviral vector, a lentiviral vector, an adenoviral vector, an adeno-associated virus vector, a poxvirus vector, a vaccinia virus vector or a modified vaccinia ankara (MVA) vector.

4. A collection of two or more different expression vectors, wherein the different vectors each comprise one of the polynucleotides according to claim 1 encoding a different fusion polypeptide.

5. A pharmaceutical composition comprising the polynucleotide of claim 1 and a pharmaceutically acceptable excipient.

6. A pharmaceutical composition comprising the expression vector of claim 2 and a pharmaceutically acceptable excipient.

7. A method of raising an immune response against one or more antigens and/or one or more antigenic fragments, comprising administering to a subject in need thereof the polynucleotide according to claim 1.

8. The method according to claim 7, wherein at least one immunomodulator, or at least one polynucleotide encoding the immunomodulator, or a vector or liposomal particle comprising the polynucleotide encoding the immunomodulator, is administered prior to, concomitantly with or subsequently to the administration of the polynucleotide.

9. A method of raising an immune response against one or more antigens and/or one or more antigenic fragments, comprising administering to a subject in need thereof the vector according to claim 2.

* * * * *

SEQUENCE LISTING

```
<160> NUMBER OF SEQ ID NOS: 51

<210> SEQ ID NO 1
<211> LENGTH: 281
<212> TYPE: PRT
<213> ORGANISM: Siniperca chuatsi

<400> SEQUENCE: 1

Met Ala Asp Ser Ala Glu Asp Ala Pro Met Ala Arg Gly Ser Leu Ala
1               5                   10                  15
```

```
Gly Ser Asp Glu Ala Leu Ile Leu Pro Ala Gly Pro Thr Gly Gly Ser
                20                  25                  30

Asn Ser Arg Ala Leu Lys Val Ala Gly Leu Thr Thr Leu Thr Cys Leu
            35                  40                  45

Leu Leu Ala Ser Gln Val Phe Thr Ala Tyr Met Val Phe Gly Gln Lys
 50                  55                  60

Glu Gln Ile His Thr Leu Gln Lys Asn Ser Glu Arg Met Ser Lys Gln
 65                  70                  75                  80

Leu Thr Arg Ser Ser Gln Ala Val Ala Pro Met Lys Met His Met Pro
                85                  90                  95

Met Asn Ser Leu Pro Leu Leu Met Asp Phe Thr Pro Asn Glu Asp Ser
                100                 105                 110

Lys Thr Pro Leu Thr Lys Leu Gln Asp Thr Ala Val Val Ser Val Glu
                115                 120                 125

Lys Gln Leu Lys Asp Leu Met Gln Asp Ser Gln Leu Pro Gln Phe Asn
130                 135                 140

Glu Thr Phe Leu Ala Asn Leu Gln Gly Leu Lys Gln Gln Met Asn Glu
145                 150                 155                 160

Ser Glu Trp Lys Ser Phe Glu Ser Trp Met Arg Tyr Trp Leu Ile Phe
                165                 170                 175

Gln Met Ala Gln Gln Lys Pro Val Pro Pro Thr Ala Asp Pro Ala Ser
                180                 185                 190

Leu Ile Lys Thr Lys Cys Gln Met Glu Ser Ala Pro Gly Val Ser Lys
                195                 200                 205

Ile Gly Ser Tyr Lys Pro Gln Cys Asp Glu Gln Gly Arg Tyr Lys Pro
                210                 215                 220

Met Gln Cys Trp His Ala Thr Gly Phe Cys Trp Cys Val Asp Glu Thr
225                 230                 235                 240

Gly Ala Val Ile Glu Gly Thr Thr Met Arg Gly Arg Pro Asp Cys Gln
                245                 250                 255

Arg Arg Ala Leu Ala Pro Arg Arg Met Ala Phe Ala Pro Ser Leu Met
                260                 265                 270

Gln Lys Thr Ile Ser Ile Asp Asp Gln
                275                 280

<210> SEQ ID NO 2
<211> LENGTH: 280
<212> TYPE: PRT
<213> ORGANISM: Dicentrarchusn labrax

<400> SEQUENCE: 2

Met Ala His Ser Glu Asp Ala Pro Leu Ala Thr Gly Ser Leu Ala Gly
 1               5                  10                  15

Ser Glu Glu Ala Leu Val Leu Ser Gly Arg Pro Thr Gly Gly Ser Asn
                20                  25                  30

Ser Arg Ala Leu Lys Ile Ala Gly Leu Thr Thr Leu Ala Cys Leu Leu
            35                  40                  45

Leu Ala Ser Gln Val Phe Thr Ala Tyr Met Val Phe Gly Gln Lys Glu
 50                  55                  60

Gln Ile His Thr Leu Gln Lys Asn Ser Glu Arg Met Thr Lys Gln Leu
 65                  70                  75                  80

Thr Arg Ser Ser Gln Ala Val Ala Pro Val Arg Met His Met Pro Met
                85                  90                  95
```

```
Ser Ser Leu Pro Met Leu Met Asp Phe Thr Asp Glu Asp Ser Lys Ala
            100                 105                 110

Thr Lys Thr Pro Leu Thr Lys Leu Gln Asp Thr Val Val Ser Val Glu
            115                 120                 125

Lys Gln Val Lys Asp Leu Ile Gln Asp Ser Gln Leu Pro Gln Phe Asn
130                 135                 140

Glu Thr Phe Met Ala Asn Leu Gln Ser Leu Lys Gln His Ile Asn Glu
145                 150                 155                 160

Ser Glu Trp Gln Ser Phe Glu Ser Trp Met Arg Tyr Trp Leu Ile Phe
                165                 170                 175

Gln Met Ala Gln Lys Thr Pro Val Pro Pro Thr Ala Asp Pro Ala Ser
            180                 185                 190

Leu Ile Lys Thr Lys Cys Gln Met Glu Ala Ala Pro Gly Pro Ser Lys
            195                 200                 205

Ile Gly Ser Tyr Lys Pro Gln Cys Asp Glu Gln Gly Arg Tyr Lys Pro
            210                 215                 220

Met Gln Cys Trp His Ala Thr Gly Tyr Cys Trp Cys Val Asp Glu Thr
225                 230                 235                 240

Gly Thr Ala Ile Glu Gly Thr Thr Met Arg Gly Arg Pro Asp Cys Gln
                245                 250                 255

Arg Gly Ser Met Pro Arg Arg Val Met Leu Ala Pro Arg Leu Met Gln
            260                 265                 270

Lys Thr Leu Ser Phe Asp Asp Gln
            275                 280

<210> SEQ ID NO 3
<211> LENGTH: 279
<212> TYPE: PRT
<213> ORGANISM: Monopterus albus

<400> SEQUENCE: 3

Met Ala Asp Ser Gln Glu Asp Ala Pro Leu Ala Arg Gly Ser Val Ala
1               5                   10                  15

Gly Ser Glu Glu Ala Leu Val Leu Pro Val Ala Pro Arg Gly Gly Ser
            20                  25                  30

Asn Ser Arg Ala Leu Lys Ile Ala Gly Leu Thr Thr Leu Ala Cys Leu
            35                  40                  45

Leu Leu Ala Ser Gln Val Phe Thr Ala Tyr Met Val Phe Asp Gln Lys
        50                  55                  60

Gln Gln Ile His Thr Leu Gln Lys Asn Ser Glu Arg Met Ser Arg Gln
65                  70                  75                  80

Met Thr Arg Thr Ser Gln Ala Val Ala Pro Val Lys Met His Leu Pro
                85                  90                  95

Met Asn Ser Leu Pro Met Leu Met Asp Tyr Thr Ser Asn Glu Asp Pro
            100                 105                 110

Lys Glu Thr Lys Thr Pro Leu Thr Lys Leu Gln Asp Thr Ala Val Val
            115                 120                 125

Ser Val Glu Asp Gln Leu Lys Glu Leu Ile Gln Asp Ala Gln Leu Pro
        130                 135                 140

Glu Phe Asn Glu Thr Phe Met Asp Asn Met Gln Arg Leu Lys Gln Leu
145                 150                 155                 160

Thr Asn Asp Ser Glu Trp Lys Ser Phe Glu Thr Trp Met Arg Tyr Trp
                165                 170                 175
```

```
Leu Ile Phe Lys Met Ser Gln Gln Lys Pro Thr Ala Pro Thr Thr Glu
                180                 185                 190

Gln Ala Met Thr Lys Cys Gln Arg Glu Ala Lys Glu Gly Leu Ile Gly
            195                 200                 205

Ser Tyr Lys Pro Gln Cys Asp Glu Gln Gly His Tyr Met Pro Met Gln
        210                 215                 220

Cys Trp His Gly Thr Gly Tyr Cys Trp Cys Val Asp Gly Ser Gly Thr
225                 230                 235                 240

Pro Ile Pro Gly Thr Lys Met Arg Gly Arg Pro Gln Cys Pro Arg Ala
                245                 250                 255

Thr Ala Ser Arg His Ala Met Arg Ser Pro Phe Leu Met Gln Arg Thr
            260                 265                 270

Val Gly Ile Asp Asp Glu Lys
        275

<210> SEQ ID NO 4
<211> LENGTH: 284
<212> TYPE: PRT
<213> ORGANISM: Oreochromis niloticus

<400> SEQUENCE: 4

Met Ala His Ser Gln Asp Asp Ala Pro Leu Ala Arg Gly Ser Leu Ala
1               5                   10                  15

Asp Ser Glu Glu Ile Leu Leu Pro Pro Ala Ala Pro Arg Gly Gly Ser
                20                  25                  30

Asn Ser Arg Ala Leu Lys Ile Ala Gly Leu Thr Thr Leu Ala Cys Leu
            35                  40                  45

Leu Val Ala Ser Gln Val Phe Thr Ala Tyr Thr Val Phe Ser Gln Lys
        50                  55                  60

Gln Gln Ile His Thr Leu Gln Lys Asn Ser Asp Arg Met Asn Lys Gln
65                  70                  75                  80

Leu Thr Arg Ser Ser His Ala Val Ala Pro Val Arg Met Ala Met Pro
                85                  90                  95

Met Asn Ser Leu Pro Leu Leu Met Asp Phe Thr Glu Asp Ser Thr Ala
                100                 105                 110

Pro Lys Thr Pro Leu Thr Lys Leu Gln Asp Thr Ala Ile Val Ser Val
            115                 120                 125

Glu Lys Gln Leu Met Asp Leu Met Gln Asp Ser Glu Leu Pro Gln Phe
        130                 135                 140

Asn Glu Thr Phe Leu Ala Asn Leu Gln Thr Leu Lys Gln His Met Asn
145                 150                 155                 160

Asp Ser Glu Trp Lys Ser Phe Glu Thr Trp Met Arg Tyr Trp Leu Ile
                165                 170                 175

Phe Lys Met Ala Gln Gln Gln Pro Ala Thr Pro Thr Pro Gln Ser Ala
            180                 185                 190

Thr Thr Ile Lys Thr Lys Cys Gln Val Glu Ala Gly Pro Gly Pro Ser
        195                 200                 205

Lys Ile Gly Ser Tyr Lys Pro Gln Cys Asp Glu Gln Gly Arg Tyr Lys
        210                 215                 220

Pro Met Gln Cys Trp His Ala Thr Gly Tyr Cys Trp Cys Val Asp Gly
225                 230                 235                 240

Glu Gly His Pro Ile Glu Gly Thr Thr Met Arg Gly Arg Pro Asp Cys
                245                 250                 255
```

```
Gln Arg Ala Ala Phe Pro Arg Arg Met Met Val Ala Pro Arg Leu Met
        260                 265                 270

Gln Lys Thr Tyr Asp Met Asp Glu Lys Gln Lys
    275                 280
```

<210> SEQ ID NO 5
<211> LENGTH: 282
<212> TYPE: PRT
<213> ORGANISM: Lates calcarifer

<400> SEQUENCE: 5

```
Met Ala His Asn Pro Glu Asp Ala Pro Leu Ala Arg Gly Ser Leu Ala
1               5                   10                  15

Gly Ser Glu Glu Asp Leu Val Val Pro Ala Gly Pro Arg Gly Gly Ser
            20                  25                  30

Asn Ser Arg Ala Leu Lys Val Ala Ala Leu Thr Thr Leu Ala Cys Leu
        35                  40                  45

Leu Leu Ser Ser Gln Val Phe Thr Ala Tyr Met Val Phe Ser Gln Lys
    50                  55                  60

Gln Gln Ile His Thr Leu Gln Lys Asn Ser Glu Arg Leu Gly Lys Gln
65                  70                  75                  80

Met Thr Arg Ser Ser Gln Ala Val Ala Pro Val Arg Met Gln Met Pro
                85                  90                  95

Met Ser Ser Leu Pro Leu Met Met Asp Phe Thr Thr Asp Glu Asp Thr
            100                 105                 110

Lys Thr Ser Lys Thr Pro Leu Thr Lys Leu Gln Asp Thr Ala Ile Val
        115                 120                 125

Ser Val Glu Lys Gln Leu Lys Asp Leu Leu Gln Asp Ala Gln Leu Pro
    130                 135                 140

Gln Phe Asn Glu Thr Phe Gln Ala Asn Leu Gln Ser Leu Lys Gln Gln
145                 150                 155                 160

Ile Asn Glu Ser Glu Trp Lys Ser Phe Glu Ser Trp Met Arg Tyr Trp
                165                 170                 175

Leu Ile Phe Gln Met Ala Gln Gln Lys Pro Val Pro Pro Thr Ser Gln
            180                 185                 190

Pro Ala Thr Lys Ile Met Thr Lys Cys Gln Leu Glu Ala Ala Pro Gly
        195                 200                 205

Ala Gly Lys Ile Gly Ser Tyr Lys Pro Gln Cys Asp Glu Gln Gly Arg
    210                 215                 220

Tyr Leu Pro Met Gln Cys Trp Tyr Pro Thr Gly Phe Cys Trp Cys Val
225                 230                 235                 240

Asp Gln Thr Gly Lys Val Ile Glu Gly Thr Ser Met Arg Gly Arg Pro
                245                 250                 255

Asp Cys Gln Arg Gly Val Pro Arg Arg Met Met Phe Ala Pro Arg Leu
            260                 265                 270

Met Gln Lys Thr Leu Ala Val Asp Asp Glu
        275                 280
```

<210> SEQ ID NO 6
<211> LENGTH: 282
<212> TYPE: PRT
<213> ORGANISM: Oryzias latipes

<400> SEQUENCE: 6

```
Met Ala Asn Thr Ala Glu Asp Ala Ser Leu Ala Ala Glu Asp Val Ser
1               5                   10                  15
```

Gly Ser Glu Glu Asn Leu Ile His Arg Val His Arg Gly Gly Ser
                20                  25                  30

Asn Ser Arg Ala Phe Lys Ile Ala Gly Leu Thr Thr Leu Ala Cys Leu
            35                  40                  45

Leu Leu Ala Ser Gln Val Phe Thr Ala Tyr Met Val Phe Asn Gln Lys
        50                  55                  60

Gln Gln Ile His Thr Leu Gln Lys Ser Glu Arg Met Gly Lys Gln
65                  70                  75                  80

Leu Thr Arg Ala Ser Gln Ala Val Ala Pro Ala Arg Met Ala Met Pro
                85                  90                  95

Met Asn Ser Leu Pro Leu Val Ser Asp Phe Ser Glu Asp Ala Lys Thr
            100                 105                 110

Pro Leu Thr Lys Leu Gln Asn Thr Ala Val Val Ser Val Glu Lys Gln
        115                 120                 125

Leu Met Asp Leu Met Gln Asp Phe Ser Leu Pro Lys Phe Asn Glu Thr
    130                 135                 140

Phe Gln Ala Asn Leu Glu Thr Leu Arg Gln Gln Val Asn Glu Ser Glu
145                 150                 155                 160

Trp Gln Thr Phe Glu Thr Trp Met Arg Tyr Trp Leu Ile Phe Gln Met
                165                 170                 175

Ala Gln Lys Gln Pro Pro Ala Pro Thr Pro Gln Pro Ala Ser Met Ile
            180                 185                 190

Lys Thr Lys Cys Gln Leu Glu Ala Ala Pro Asp Thr Ile Ser Lys Ile
        195                 200                 205

Gly Thr Tyr Lys Pro Gln Cys Asp Glu Gln Gly Lys Tyr Lys Ala Met
    210                 215                 220

Gln Cys Trp His Ala Thr Gly Tyr Cys Trp Cys Val Asp Glu Ser Gly
225                 230                 235                 240

Asn Pro Ile Glu Gly Thr Thr Met Arg Gly Arg Pro Asp Cys Arg Arg
                245                 250                 255

Gly Leu Ala Pro Tyr Arg Met Met Val Gln Pro Arg Leu Met Gln Arg
            260                 265                 270

Thr Phe Leu Asp Asp Glu Lys Lys Asp Lys
        275                 280

<210> SEQ ID NO 7
<211> LENGTH: 27
<212> TYPE: PRT
<213> ORGANISM: Siniperca chuatsi

<400> SEQUENCE: 7

Gly Gln Lys Glu Gln Ile His Thr Leu Gln Lys Asn Ser Glu Arg Met
1               5                   10                  15

Ser Lys Gln Leu Thr Arg Ser Ser Gln Ala Val
            20                  25

<210> SEQ ID NO 8
<211> LENGTH: 27
<212> TYPE: PRT
<213> ORGANISM: Dicentrarchus labrax

<400> SEQUENCE: 8

Gly Gln Lys Glu Gln Ile His Thr Leu Gln Lys Asn Ser Glu Arg Met
1               5                   10                  15

Thr Lys Gln Leu Thr Arg Ser Ser Gln Ala Val
            20                  25

<210> SEQ ID NO 9
<211> LENGTH: 27
<212> TYPE: PRT
<213> ORGANISM: Monopterus albus

<400> SEQUENCE: 9

Asp Gln Lys Gln Gln Ile His Thr Leu Gln Lys Asn Ser Glu Arg Met
1               5                   10                  15

Ser Arg Gln Met Thr Arg Thr Ser Gln Ala Val
            20                  25

<210> SEQ ID NO 10
<211> LENGTH: 27
<212> TYPE: PRT
<213> ORGANISM: Oreochromis niloticus

<400> SEQUENCE: 10

Ser Gln Lys Gln Gln Ile His Thr Leu Gln Lys Asn Ser Asp Arg Met
1               5                   10                  15

Asn Lys Gln Leu Thr Arg Ser Ser His Ala Val
            20                  25

<210> SEQ ID NO 11
<211> LENGTH: 27
<212> TYPE: PRT
<213> ORGANISM: Lates calcarifer

<400> SEQUENCE: 11

Ser Gln Lys Gln Gln Ile His Thr Leu Gln Lys Asn Ser Glu Arg Leu
1               5                   10                  15

Gly Lys Gln Met Thr Arg Ser Ser Gln Ala Val
            20                  25

<210> SEQ ID NO 12
<211> LENGTH: 27
<212> TYPE: PRT
<213> ORGANISM: Oryzias latipes

<400> SEQUENCE: 12

Asn Gln Lys Gln Gln Ile His Thr Leu Gln Lys Ser Ser Glu Arg Met
1               5                   10                  15

Gly Lys Gln Leu Thr Arg Ala Ser Gln Ala Val
            20                  25

<210> SEQ ID NO 13
<211> LENGTH: 16
<212> TYPE: PRT
<213> ORGANISM: Siniperca chuatsi

<400> SEQUENCE: 13

Gln Ile His Thr Leu Gln Lys Asn Ser Glu Arg Met Ser Lys Gln Leu
1               5                   10                  15

<210> SEQ ID NO 14
<211> LENGTH: 16
<212> TYPE: PRT
<213> ORGANISM: Dicentrarchus labrax

<400> SEQUENCE: 14

Gln Ile His Thr Leu Gln Lys Asn Ser Glu Arg Met Thr Lys Gln Leu
1               5                   10                  15

<210> SEQ ID NO 15
<211> LENGTH: 16
<212> TYPE: PRT
<213> ORGANISM: Monopterus albus

<400> SEQUENCE: 15

Gln Ile His Thr Leu Gln Lys Asn Ser Glu Arg Met Ser Arg Gln Met
1               5                   10                  15

<210> SEQ ID NO 16
<211> LENGTH: 16
<212> TYPE: PRT
<213> ORGANISM: Oreochromis niloticus

<400> SEQUENCE: 16

Gln Ile His Thr Leu Gln Lys Asn Ser Asp Arg Met Asn Lys Gln Leu
1               5                   10                  15

<210> SEQ ID NO 17
<211> LENGTH: 16
<212> TYPE: PRT
<213> ORGANISM: Lates calcarifer

<400> SEQUENCE: 17

Gln Ile His Thr Leu Gln Lys Asn Ser Glu Arg Leu Gly Lys Gln Met
1               5                   10                  15

<210> SEQ ID NO 18
<211> LENGTH: 16
<212> TYPE: PRT
<213> ORGANISM: Oryzias latipes

<400> SEQUENCE: 18

Gln Ile His Thr Leu Gln Lys Ser Ser Glu Arg Met Gly Lys Gln Leu
1               5                   10                  15

<210> SEQ ID NO 19
<211> LENGTH: 81
<212> TYPE: PRT
<213> ORGANISM: Siniperca chuatsi

<400> SEQUENCE: 19

Met Ala Asp Ser Ala Glu Asp Ala Pro Met Ala Arg Gly Ser Leu Ala
1               5                   10                  15

Gly Ser Asp Glu Ala Leu Ile Leu Pro Ala Gly Pro Thr Gly Gly Ser
                20                  25                  30

Asn Ser Arg Ala Leu Lys Val Ala Gly Leu Thr Thr Leu Thr Cys Leu
            35                  40                  45

Leu Leu Ala Ser Gln Val Phe Thr Ala Tyr Met Val Phe Gly Gln Lys
        50                  55                  60

Glu Gln Ile His Thr Leu Gln Lys Asn Ser Glu Arg Met Ser Lys Gln
65                  70                  75                  80

Leu

<210> SEQ ID NO 20
<211> LENGTH: 25
<212> TYPE: PRT
<213> ORGANISM: Homo sapiens

<400> SEQUENCE: 20

Leu Leu Pro Phe Tyr Pro Pro Asp Glu Ala Leu Glu Ile Gly Leu Glu
1               5                   10                  15

```
Leu Asn Ser Ser Ala Leu Pro Pro Thr
            20                  25

<210> SEQ ID NO 21
<211> LENGTH: 25
<212> TYPE: PRT
<213> ORGANISM: Homo sapiens

<400> SEQUENCE: 21

Ile Leu Pro Gln Ala Pro Ser Gly Pro Ser Tyr Ala Thr Tyr Leu Gln
1               5                   10                  15

Pro Ala Gln Ala Gln Met Leu Thr Pro
            20                  25

<210> SEQ ID NO 22
<211> LENGTH: 25
<212> TYPE: PRT
<213> ORGANISM: Homo sapiens

<400> SEQUENCE: 22

Lys Pro Leu Arg Arg Asn Asn Ser Tyr Thr Ser Tyr Ile Met Ala Ile
1               5                   10                  15

Cys Gly Met Pro Leu Asp Ser Phe Arg
            20                  25

<210> SEQ ID NO 23
<211> LENGTH: 25
<212> TYPE: PRT
<213> ORGANISM: Homo sapiens

<400> SEQUENCE: 23

Val Ile Gln Thr Ser Lys Tyr Tyr Met Arg Asp Val Ile Ala Ile Glu
1               5                   10                  15

Ser Ala Trp Leu Leu Glu Leu Ala Pro
            20                  25

<210> SEQ ID NO 24
<211> LENGTH: 25
<212> TYPE: PRT
<213> ORGANISM: Homo sapiens

<400> SEQUENCE: 24

His Ile His Arg Ala Gly Gly Leu Phe Val Ala Asp Ala Ile Gln Val
1               5                   10                  15

Gly Phe Gly Arg Ile Gly Lys His Phe
            20                  25

<210> SEQ ID NO 25
<211> LENGTH: 137
<212> TYPE: PRT
<213> ORGANISM: Artificial Sequence
<220> FEATURE:
<223> OTHER INFORMATION: Multimeres of human antigens

<400> SEQUENCE: 25

Met Leu Leu Pro Phe Tyr Pro Pro Asp Glu Ala Leu Glu Ile Gly Leu
1               5                   10                  15

Glu Leu Asn Ser Ser Ala Leu Pro Pro Thr Ile Leu Pro Gln Ala Pro
            20                  25                  30

Ser Gly Pro Ser Tyr Ala Thr Tyr Leu Gln Pro Ala Gln Ala Gln Met
        35                  40                  45
```

-continued

```
Leu Thr Pro Lys Pro Leu Arg Arg Asn Asn Ser Tyr Thr Ser Tyr Ile
    50                  55                  60
Met Ala Ile Cys Gly Met Pro Leu Asp Ser Phe Arg Val Ile Gln Thr
 65                  70                  75                  80
Ser Lys Tyr Tyr Met Arg Asp Val Ile Ala Ile Glu Ser Ala Trp Leu
                 85                  90                  95
Leu Glu Leu Ala Pro His Ile His Arg Ala Gly Gly Leu Phe Val Ala
            100                 105                 110
Asp Ala Ile Gln Val Gly Phe Gly Arg Ile Gly Lys His Phe Gly Tyr
        115                 120                 125
Pro Tyr Asp Val Pro Asp Tyr Ala Ser
    130                 135
```

<210> SEQ ID NO 26
<211> LENGTH: 417
<212> TYPE: PRT
<213> ORGANISM: Artificial Sequence
<220> FEATURE:
<223> OTHER INFORMATION: Fusion protein of Siniperca chuatsi full length
      invariant chain and multimeric antigen

<400> SEQUENCE: 26

```
Met Ala Asp Ser Ala Glu Asp Ala Pro Met Ala Arg Gly Ser Leu Ala
 1               5                  10                  15
Gly Ser Asp Glu Ala Leu Ile Leu Pro Ala Gly Pro Thr Gly Gly Ser
             20                  25                  30
Asn Ser Arg Ala Leu Lys Val Ala Gly Leu Thr Thr Leu Thr Cys Leu
         35                  40                  45
Leu Leu Ala Ser Gln Val Phe Thr Ala Tyr Met Val Phe Gly Gln Lys
    50                  55                  60
Glu Gln Ile His Thr Leu Gln Lys Asn Ser Glu Arg Met Ser Lys Gln
 65                  70                  75                  80
Leu Thr Arg Ser Ser Gln Ala Val Ala Pro Met Lys Met His Met Pro
                 85                  90                  95
Met Asn Ser Leu Pro Leu Leu Met Asp Phe Thr Pro Asn Glu Asp Ser
            100                 105                 110
Lys Thr Pro Leu Thr Lys Leu Gln Asp Thr Ala Val Val Ser Val Glu
        115                 120                 125
Lys Gln Leu Lys Asp Leu Met Gln Asp Ser Gln Leu Pro Gln Phe Asn
    130                 135                 140
Glu Thr Phe Leu Ala Asn Leu Gln Gly Leu Lys Gln Gln Met Asn Glu
145                 150                 155                 160
Ser Glu Trp Lys Ser Phe Glu Ser Trp Met Arg Tyr Trp Leu Ile Phe
                165                 170                 175
Gln Met Ala Gln Gln Lys Pro Val Pro Pro Thr Ala Asp Pro Ala Ser
            180                 185                 190
Leu Ile Lys Thr Lys Cys Gln Met Glu Ser Ala Pro Gly Val Ser Lys
        195                 200                 205
Ile Gly Ser Tyr Lys Pro Gln Cys Asp Glu Gln Gly Arg Tyr Lys Pro
    210                 215                 220
Met Gln Cys Trp His Ala Thr Gly Phe Cys Trp Cys Val Asp Glu Thr
225                 230                 235                 240
Gly Ala Val Ile Glu Gly Thr Thr Met Arg Gly Arg Pro Asp Cys Gln
                245                 250                 255
Arg Arg Ala Leu Ala Pro Arg Arg Met Ala Phe Ala Pro Ser Leu Met
            260                 265                 270
```

```
Gln Lys Thr Ile Ser Ile Asp Asp Gln Leu Leu Pro Phe Tyr Pro Pro
            275                 280                 285

Asp Glu Ala Leu Glu Ile Gly Leu Glu Leu Asn Ser Ser Ala Leu Pro
290                 295                 300

Pro Thr Ile Leu Pro Gln Ala Pro Ser Gly Pro Ser Tyr Ala Thr Tyr
305                 310                 315                 320

Leu Gln Pro Ala Gln Ala Gln Met Leu Thr Pro Lys Pro Leu Arg Arg
                325                 330                 335

Asn Asn Ser Tyr Thr Ser Tyr Ile Met Ala Ile Cys Gly Met Pro Leu
            340                 345                 350

Asp Ser Phe Arg Val Ile Gln Thr Ser Lys Tyr Tyr Met Arg Asp Val
            355                 360                 365

Ile Ala Ile Glu Ser Ala Trp Leu Leu Glu Leu Ala Pro His Ile His
370                 375                 380

Arg Ala Gly Gly Leu Phe Val Ala Asp Ala Ile Gln Val Gly Phe Gly
385                 390                 395                 400

Arg Ile Gly Lys His Phe Gly Tyr Pro Tyr Asp Val Pro Asp Tyr Ala
                405                 410                 415

Ser
```

<210> SEQ ID NO 27
<211> LENGTH: 217
<212> TYPE: PRT
<213> ORGANISM: Artificial Sequence
<220> FEATURE:
<223> OTHER INFORMATION: Fusion protein of Siniperca chuatsi invariant
      chain fragment and multimeric antigen

<400> SEQUENCE: 27

```
Met Ala Asp Ser Ala Glu Asp Ala Pro Met Ala Arg Gly Ser Leu Ala
1               5                   10                  15

Gly Ser Asp Glu Ala Leu Ile Leu Pro Ala Gly Pro Thr Gly Gly Ser
            20                  25                  30

Asn Ser Arg Ala Leu Lys Val Ala Gly Leu Thr Thr Leu Thr Cys Leu
        35                  40                  45

Leu Leu Ala Ser Gln Val Phe Thr Ala Tyr Met Val Phe Gly Gln Lys
    50                  55                  60

Glu Gln Ile His Thr Leu Gln Lys Asn Ser Glu Arg Met Ser Lys Gln
65                  70                  75                  80

Leu Leu Leu Pro Phe Tyr Pro Pro Asp Glu Ala Leu Glu Ile Gly Leu
                85                  90                  95

Glu Leu Asn Ser Ser Ala Leu Pro Pro Thr Ile Leu Pro Gln Ala Pro
            100                 105                 110

Ser Gly Pro Ser Tyr Ala Thr Tyr Leu Gln Pro Ala Gln Ala Gln Met
        115                 120                 125

Leu Thr Pro Lys Pro Leu Arg Arg Asn Asn Ser Tyr Thr Ser Tyr Ile
    130                 135                 140

Met Ala Ile Cys Gly Met Pro Leu Asp Ser Phe Arg Val Ile Gln Thr
145                 150                 155                 160

Ser Lys Tyr Tyr Met Arg Asp Val Ile Ala Ile Glu Ser Ala Trp Leu
                165                 170                 175

Leu Glu Leu Ala Pro His Ile His Arg Ala Gly Gly Leu Phe Val Ala
            180                 185                 190

Asp Ala Ile Gln Val Gly Phe Gly Arg Ile Gly Lys His Phe Gly Tyr
        195                 200                 205
```

```
Pro Tyr Asp Val Pro Asp Tyr Ala Ser
    210             215
```

<210> SEQ ID NO 28
<211> LENGTH: 164
<212> TYPE: PRT
<213> ORGANISM: Artificial Sequence
<220> FEATURE:
<223> OTHER INFORMATION: Fusion protein of Siniperca chuatsi invariant
      chain fragment and multimeric antigen

<400> SEQUENCE: 28

```
Met Gly Gln Lys Glu Gln Ile His Thr Leu Gln Lys Asn Ser Glu Arg
1               5                   10                  15

Met Ser Lys Gln Leu Thr Arg Ser Ser Gln Ala Val Leu Leu Pro Phe
            20                  25                  30

Tyr Pro Pro Asp Glu Ala Leu Glu Ile Gly Leu Glu Leu Asn Ser Ser
        35                  40                  45

Ala Leu Pro Pro Thr Ile Leu Pro Gln Ala Pro Ser Gly Pro Ser Tyr
50                  55                  60

Ala Thr Tyr Leu Gln Pro Ala Gln Ala Gln Met Leu Thr Pro Lys Pro
65                  70                  75                  80

Leu Arg Arg Asn Asn Ser Tyr Thr Ser Tyr Ile Met Ala Ile Cys Gly
                85                  90                  95

Met Pro Leu Asp Ser Phe Arg Val Ile Gln Thr Ser Lys Tyr Tyr Met
            100                 105                 110

Arg Asp Val Ile Ala Ile Glu Ser Ala Trp Leu Leu Glu Leu Ala Pro
        115                 120                 125

His Ile His Arg Ala Gly Gly Leu Phe Val Ala Asp Ala Ile Gln Val
    130                 135                 140

Gly Phe Gly Arg Ile Gly Lys His Phe Gly Tyr Pro Tyr Asp Val Pro
145                 150                 155                 160

Asp Tyr Ala Ser
```

<210> SEQ ID NO 29
<211> LENGTH: 153
<212> TYPE: PRT
<213> ORGANISM: Artificial Sequence
<220> FEATURE:
<223> OTHER INFORMATION: Fusion protein of Siniperca chuatsi invariant
      chain fragment and multimeric antigen

<400> SEQUENCE: 29

```
Met Gln Ile His Thr Leu Gln Lys Asn Ser Glu Arg Met Ser Lys Gln
1               5                   10                  15

Leu Leu Leu Pro Phe Tyr Pro Pro Asp Glu Ala Leu Glu Ile Gly Leu
            20                  25                  30

Glu Leu Asn Ser Ser Ala Leu Pro Pro Thr Ile Leu Pro Gln Ala Pro
        35                  40                  45

Ser Gly Pro Ser Tyr Ala Thr Tyr Leu Gln Pro Ala Gln Ala Gln Met
    50                  55                  60

Leu Thr Pro Lys Pro Leu Arg Arg Asn Asn Ser Tyr Thr Ser Tyr Ile
65                  70                  75                  80

Met Ala Ile Cys Gly Met Pro Leu Asp Ser Phe Arg Val Ile Gln Thr
                85                  90                  95

Ser Lys Tyr Tyr Met Arg Asp Val Ile Ala Ile Glu Ser Ala Trp Leu
            100                 105                 110
```

```
Leu Glu Leu Ala Pro His Ile His Arg Ala Gly Gly Leu Phe Val Ala
            115                 120                 125

Asp Ala Ile Gln Val Gly Phe Gly Arg Ile Gly Lys His Phe Gly Tyr
        130                 135                 140

Pro Tyr Asp Val Pro Asp Tyr Ala Ser
145                 150

<210> SEQ ID NO 30
<211> LENGTH: 11
<212> TYPE: PRT
<213> ORGANISM: Influenza A virus

<400> SEQUENCE: 30

Gly Tyr Pro Tyr Asp Val Pro Asp Tyr Ala Ser
1               5                   10

<210> SEQ ID NO 31
<211> LENGTH: 27
<212> TYPE: PRT
<213> ORGANISM: Artificial Sequence
<220> FEATURE:
<223> OTHER INFORMATION: Generic sequence
<220> FEATURE:
<221> NAME/KEY: MISC_FEATURE
<222> LOCATION: (1)..(1)
<223> OTHER INFORMATION: Xaa is G, D, S or N
<220> FEATURE:
<221> NAME/KEY: MISC_FEATURE
<222> LOCATION: (4)..(4)
<223> OTHER INFORMATION: Xaa is E or Q
<220> FEATURE:
<221> NAME/KEY: MISC_FEATURE
<222> LOCATION: (12)..(12)
<223> OTHER INFORMATION: Xaa is N or S
<220> FEATURE:
<221> NAME/KEY: MISC_FEATURE
<222> LOCATION: (14)..(14)
<223> OTHER INFORMATION: Xaa is D or E
<220> FEATURE:
<221> NAME/KEY: MISC_FEATURE
<222> LOCATION: (16)..(16)
<223> OTHER INFORMATION: Xaa is M or L
<220> FEATURE:
<221> NAME/KEY: MISC_FEATURE
<222> LOCATION: (17)..(17)
<223> OTHER INFORMATION: Xaa is G, N, S or T
<220> FEATURE:
<221> NAME/KEY: MISC_FEATURE
<222> LOCATION: (18)..(18)
<223> OTHER INFORMATION: Xaa is K or R
<220> FEATURE:
<221> NAME/KEY: MISC_FEATURE
<222> LOCATION: (20)..(20)
<223> OTHER INFORMATION: Xaa is L or M
<220> FEATURE:
<221> NAME/KEY: MISC_FEATURE
<222> LOCATION: (23)..(23)
<223> OTHER INFORMATION: Xaa is S, T or A
<220> FEATURE:
<221> NAME/KEY: MISC_FEATURE
<222> LOCATION: (25)..(25)
<223> OTHER INFORMATION: Xaa is Q or H

<400> SEQUENCE: 31

Xaa Gln Lys Xaa Gln Ile His Thr Leu Gln Lys Xaa Ser Xaa Arg Xaa
1               5                   10                  15

Xaa Xaa Gln Xaa Thr Arg Xaa Ser Xaa Ala Val
            20                  25

<210> SEQ ID NO 32
<211> LENGTH: 26
```

```
<212> TYPE: PRT
<213> ORGANISM: Artificial Sequence
<220> FEATURE:
<223> OTHER INFORMATION: Generic sequence
<220> FEATURE:
<221> NAME/KEY: MISC_FEATURE
<222> LOCATION: (2)..(2)
<223> OTHER INFORMATION: Xaa is L or F
<220> FEATURE:
<221> NAME/KEY: MISC_FEATURE
<222> LOCATION: (4)..(4)
<223> OTHER INFORMATION: Xaa is I or V
<220> FEATURE:
<221> NAME/KEY: MISC_FEATURE
<222> LOCATION: (6)..(6)
<223> OTHER INFORMATION: Xaa is G or A
<220> FEATURE:
<221> NAME/KEY: MISC_FEATURE
<222> LOCATION: (11)..(11)
<223> OTHER INFORMATION: Xaa is T or A
<220> FEATURE:
<221> NAME/KEY: MISC_FEATURE
<222> LOCATION: (15)..(15)
<223> OTHER INFORMATION: Xaa is L or V
<220> FEATURE:
<221> NAME/KEY: MISC_FEATURE
<222> LOCATION: (16)..(16)
<223> OTHER INFORMATION: Xaa is A or S
<220> FEATURE:
<221> NAME/KEY: MISC_FEATURE
<222> LOCATION: (24)..(24)
<223> OTHER INFORMATION: Xaa is M or T

<400> SEQUENCE: 32

Ala Xaa Lys Xaa Ala Xaa Leu Thr Thr Leu Xaa Cys Leu Leu Xaa Xaa
1               5                   10                  15

Ser Gln Val Phe Thr Ala Tyr Xaa Val Phe
            20                  25

<210> SEQ ID NO 33
<211> LENGTH: 19
<212> TYPE: PRT
<213> ORGANISM: Artificial Sequence
<220> FEATURE:
<223> OTHER INFORMATION: Generic sequence
<220> FEATURE:
<221> NAME/KEY: MISC_FEATURE
<222> LOCATION: (3)..(3)
<223> OTHER INFORMATION: Xaa is M, V or A
<220> FEATURE:
<221> NAME/KEY: MISC_FEATURE
<222> LOCATION: (4)..(4)
<223> OTHER INFORMATION: Xaa is R or K
<220> FEATURE:
<221> NAME/KEY: MISC_FEATURE
<222> LOCATION: (6)..(6)
<223> OTHER INFORMATION: Xaa is H, A or Q
<220> FEATURE:
<221> NAME/KEY: MISC_FEATURE
<222> LOCATION: (7)..(7)
<223> OTHER INFORMATION: Xaa is M or L
<220> FEATURE:
<221> NAME/KEY: MISC_FEATURE
<222> LOCATION: (10)..(10)
<223> OTHER INFORMATION: Xaa is N or S
<220> FEATURE:
<221> NAME/KEY: MISC_FEATURE
<222> LOCATION: (14)..(14)
<223> OTHER INFORMATION: Xaa is M or L
<220> FEATURE:
<221> NAME/KEY: MISC_FEATURE
<222> LOCATION: (15)..(15)
<223> OTHER INFORMATION: Xaa is M, L or V
<220> FEATURE:
<221> NAME/KEY: MISC_FEATURE
<222> LOCATION: (16)..(16)
```

<223> OTHER INFORMATION: Xaa is M or S
<220> FEATURE:
<221> NAME/KEY: MISC_FEATURE
<222> LOCATION: (18)..(18)
<223> OTHER INFORMATION: Xaa is F or Y
<220> FEATURE:
<221> NAME/KEY: MISC_FEATURE
<222> LOCATION: (19)..(19)
<223> OTHER INFORMATION: Xaa is T or S

<400> SEQUENCE: 33

Ala Pro Xaa Xaa Met Xaa Xaa Pro Met Xaa Ser Leu Pro Xaa Xaa Xaa
1               5                   10                  15

Asp Xaa Xaa

<210> SEQ ID NO 34
<211> LENGTH: 25
<212> TYPE: PRT
<213> ORGANISM: Mus musculus

<400> SEQUENCE: 34

Leu Arg Thr Ala Ala Tyr Val Asn Ala Ile Glu Lys Ile Phe Lys Val
1               5                   10                  15

Tyr Asn Glu Ala Gly Val Thr Phe Thr
            20                  25

<210> SEQ ID NO 35
<211> LENGTH: 25
<212> TYPE: PRT
<213> ORGANISM: Mus musculus

<400> SEQUENCE: 35

Ser Asn Phe Thr Val Asp Cys Ser Lys Ala Gly Asn Asp Met Leu Leu
1               5                   10                  15

Val Gly Val His Gly Pro Arg Thr Pro
            20                  25

<210> SEQ ID NO 36
<211> LENGTH: 25
<212> TYPE: PRT
<213> ORGANISM: Mus musculus

<400> SEQUENCE: 36

Glu Ser Asp Arg Asn Lys Glu Ser Ser Asp Gln Thr Ser Val Asn Met
1               5                   10                  15

Asn Gly Leu Glu Asn Lys Ile Ser Tyr
            20                  25

<210> SEQ ID NO 37
<211> LENGTH: 25
<212> TYPE: PRT
<213> ORGANISM: Mus musculus

<400> SEQUENCE: 37

Gln Thr Ser Pro Thr Gly Ile Leu Pro Thr Thr Ser Asn Ser Ile Ser
1               5                   10                  15

Thr Ser Glu Met Thr Trp Lys Ser Ser
            20                  25

<210> SEQ ID NO 38
<211> LENGTH: 25
<212> TYPE: PRT
<213> ORGANISM: Mus musculus

```
<400> SEQUENCE: 38

Ala Val Gln Lys Leu Asn Leu Gln Asn Leu Val Ile Leu Gln Ala Pro
1               5                   10                  15

Glu Asn Leu Thr Leu Ser Asn Leu Ser
            20                  25

<210> SEQ ID NO 39
<211> LENGTH: 25
<212> TYPE: PRT
<213> ORGANISM: Mus musculus

<400> SEQUENCE: 39

Thr Ser Ile Pro Ser Val Ser Asn Ala Leu Asn Trp Lys Glu Phe Ser
1               5                   10                  15

Phe Ile Gln Ser Thr Leu Gly Tyr Val
            20                  25

<210> SEQ ID NO 40
<211> LENGTH: 25
<212> TYPE: PRT
<213> ORGANISM: Mus musculus

<400> SEQUENCE: 40

Ile Ile Gln Val Ser Pro Lys Asp Ile Gln Leu Thr Ile Phe Pro Ser
1               5                   10                  15

Lys Ser Val Lys Glu Gly Asp Thr Val
            20                  25

<210> SEQ ID NO 41
<211> LENGTH: 25
<212> TYPE: PRT
<213> ORGANISM: Mus musculus

<400> SEQUENCE: 41

His Ser Gly Gln Asn His Leu Lys Glu Met Ala Ile Ser Val Leu Glu
1               5                   10                  15

Ala Arg Ala Cys Ala Ala Ala Gly Gln
            20                  25

<210> SEQ ID NO 42
<211> LENGTH: 25
<212> TYPE: PRT
<213> ORGANISM: Mus musculus

<400> SEQUENCE: 42

Lys Ala Ser Lys Lys Gly Met Trp Ser Glu Gly Asn Ser Ser His Thr
1               5                   10                  15

Ile Arg Asp Leu Lys Tyr Thr Ile Glu
            20                  25

<210> SEQ ID NO 43
<211> LENGTH: 25
<212> TYPE: PRT
<213> ORGANISM: Mus musculus

<400> SEQUENCE: 43

Leu Pro Gly Phe Lys Gly Val Lys Gly His Ser Gly Ile Asp Gly Leu
1               5                   10                  15

Lys Gly Gln Pro Gly Ala Gln Gly Val
            20                  25
```

```
<210> SEQ ID NO 44
<211> LENGTH: 25
<212> TYPE: PRT
<213> ORGANISM: Mus musculus

<400> SEQUENCE: 44

Ala Leu Gly Ser Leu Ala Leu Met Ile Trp Leu Met Thr Thr Pro His
1               5                   10                  15

Ser His Glu Thr Glu Gln Lys Arg Leu
            20                  25

<210> SEQ ID NO 45
<211> LENGTH: 25
<212> TYPE: PRT
<213> ORGANISM: Mus musculus

<400> SEQUENCE: 45

Ser Trp Ile His Cys Trp Lys Tyr Leu Ser Val Gln Ser Gln Leu Phe
1               5                   10                  15

Arg Gly Ser Ser Leu Leu Phe Arg Arg
            20                  25

<210> SEQ ID NO 46
<211> LENGTH: 25
<212> TYPE: PRT
<213> ORGANISM: Mus musculus

<400> SEQUENCE: 46

Glu Val Ala Thr Arg Met Gln Ser Phe Gly Met Lys Ile Val Gly Tyr
1               5                   10                  15

Asp Pro Ile Ile Ser Pro Glu Val Ala
            20                  25

<210> SEQ ID NO 47
<211> LENGTH: 25
<212> TYPE: PRT
<213> ORGANISM: Mus musculus

<400> SEQUENCE: 47

Thr Val Ser Val Val Ala Leu His Asp Asp Met Glu Asn Gln Pro Leu
1               5                   10                  15

Ile Gly Ile Gln Ser Thr Ala Ile Pro
            20                  25

<210> SEQ ID NO 48
<211> LENGTH: 25
<212> TYPE: PRT
<213> ORGANISM: Mus musculus

<400> SEQUENCE: 48

Phe Pro Glu Phe Ala Arg Tyr Thr Thr Pro Glu Asp Thr Thr Pro Glu
1               5                   10                  15

Pro Gly Glu Asp Pro Arg Val Thr Arg
            20                  25

<210> SEQ ID NO 49
<211> LENGTH: 512
<212> TYPE: PRT
<213> ORGANISM: Artificial Sequence
<220> FEATURE:
<223> OTHER INFORMATION: Multimer of antigenic fragments of Mus musculus
      antigens
```

<400> SEQUENCE: 49

Met Leu Arg Thr Ala Ala Tyr Val Asn Ala Ile Glu Lys Ile Phe Lys
1               5                   10                  15

Val Tyr Asn Glu Ala Gly Val Thr Phe Thr Ser Asn Phe Thr Val Asp
                20                  25                  30

Cys Ser Lys Ala Gly Asn Asp Met Leu Leu Val Gly Val His Gly Pro
            35                  40                  45

Arg Thr Pro Ile Leu Pro Gln Ala Pro Ser Gly Pro Ser Tyr Ala Thr
        50                  55                  60

Tyr Leu Gln Pro Ala Gln Ala Gln Met Leu Thr Pro Glu Ser Asp Arg
65                  70                  75                  80

Asn Lys Glu Ser Ser Asp Gln Thr Ser Val Asn Met Asn Gly Leu Glu
                85                  90                  95

Asn Lys Ile Ser Tyr Leu Leu Pro Phe Tyr Pro Pro Asp Glu Ala Leu
            100                 105                 110

Glu Ile Gly Leu Glu Leu Asn Ser Ser Ala Leu Pro Pro Thr Gln Thr
        115                 120                 125

Ser Pro Thr Gly Ile Leu Pro Thr Thr Ser Asn Ser Ile Ser Thr Ser
    130                 135                 140

Glu Met Thr Trp Lys Ser Ser Ala Val Gln Lys Leu Asn Leu Gln Asn
145                 150                 155                 160

Leu Val Ile Leu Gln Ala Pro Glu Asn Leu Thr Leu Ser Asn Leu Ser
                165                 170                 175

Thr Ser Ile Pro Ser Val Ser Asn Ala Leu Asn Trp Lys Glu Phe Ser
            180                 185                 190

Phe Ile Gln Ser Thr Leu Gly Tyr Val Ile Gln Val Ser Pro Lys
        195                 200                 205

Asp Ile Gln Leu Thr Ile Phe Pro Ser Lys Ser Val Lys Glu Gly Asp
    210                 215                 220

Thr Val His Ile His Arg Ala Gly Gly Leu Phe Val Ala Asp Ala Ile
225                 230                 235                 240

Gln Val Gly Phe Gly Arg Ile Gly Lys His Phe His Ser Gly Gln Asn
                245                 250                 255

His Leu Lys Glu Met Ala Ile Ser Val Leu Glu Ala Arg Ala Cys Ala
            260                 265                 270

Ala Ala Gly Gln Val Ile Gln Thr Ser Lys Tyr Tyr Met Arg Asp Val
        275                 280                 285

Ile Ala Ile Glu Ser Ala Trp Leu Leu Glu Leu Ala Pro Lys Ala Ser
    290                 295                 300

Lys Lys Gly Met Trp Ser Glu Gly Asn Ser Ser His Thr Ile Arg Asp
305                 310                 315                 320

Leu Lys Tyr Thr Ile Glu Leu Pro Gly Phe Lys Gly Val Lys Gly His
                325                 330                 335

Ser Gly Ile Asp Gly Leu Lys Gly Gln Pro Gly Ala Gln Gly Val Ala
            340                 345                 350

Leu Gly Ser Leu Ala Leu Met Ile Trp Leu Met Thr Thr Pro His Ser
        355                 360                 365

His Glu Thr Glu Gln Lys Arg Leu Ser Trp Ile His Cys Trp Lys Tyr
    370                 375                 380

Leu Ser Val Gln Ser Gln Leu Phe Arg Gly Ser Ser Leu Leu Phe Arg
385                 390                 395                 400

```
Arg Lys Pro Leu Arg Arg Asn Asn Ser Tyr Thr Ser Tyr Ile Met Ala
            405                 410                 415

Ile Cys Gly Met Pro Leu Asp Ser Phe Arg Glu Val Ala Thr Arg Met
            420                 425                 430

Gln Ser Phe Gly Met Lys Ile Val Gly Tyr Asp Pro Ile Ile Ser Pro
            435                 440                 445

Glu Val Ala Thr Val Ser Val Val Ala Leu His Asp Asp Met Glu Asn
450                 455                 460

Gln Pro Leu Ile Gly Ile Gln Ser Thr Ala Ile Pro Phe Pro Glu Phe
465                 470                 475                 480

Ala Arg Tyr Thr Thr Pro Glu Asp Thr Pro Glu Pro Gly Glu Asp
            485                 490                 495

Pro Arg Val Thr Arg Gly Tyr Pro Tyr Asp Val Pro Asp Tyr Ala Ser
            500                 505                 510

<210> SEQ ID NO 50
<211> LENGTH: 539
<212> TYPE: PRT
<213> ORGANISM: Artificial Sequence
<220> FEATURE:
<223> OTHER INFORMATION: Multimer of antigenic fragments of Mus musculus
      antigens

<400> SEQUENCE: 50

Met Gly Gln Lys Glu Gln Ile His Thr Leu Gln Lys Asn Ser Glu Arg
1               5                   10                  15

Met Ser Lys Gln Leu Thr Arg Ser Ser Gln Ala Val Leu Arg Thr Ala
            20                  25                  30

Ala Tyr Val Asn Ala Ile Glu Lys Ile Phe Lys Val Tyr Asn Glu Ala
            35                  40                  45

Gly Val Thr Phe Thr Ser Asn Phe Thr Val Asp Cys Ser Lys Ala Gly
        50                  55                  60

Asn Asp Met Leu Leu Val Gly Val His Gly Pro Arg Thr Pro Ile Leu
65                  70                  75                  80

Pro Gln Ala Pro Ser Gly Pro Ser Tyr Ala Thr Tyr Leu Gln Pro Ala
            85                  90                  95

Gln Ala Gln Met Leu Thr Pro Glu Ser Asp Arg Asn Lys Glu Ser Ser
            100                 105                 110

Asp Gln Thr Ser Val Asn Met Asn Gly Leu Glu Asn Lys Ile Ser Tyr
        115                 120                 125

Leu Leu Pro Phe Tyr Pro Pro Asp Glu Ala Leu Glu Ile Gly Leu Glu
130                 135                 140

Leu Asn Ser Ser Ala Leu Pro Pro Thr Gln Thr Ser Pro Thr Gly Ile
145                 150                 155                 160

Leu Pro Thr Thr Ser Asn Ser Ile Ser Thr Ser Glu Met Thr Trp Lys
            165                 170                 175

Ser Ser Ala Val Gln Lys Leu Asn Leu Gln Asn Leu Val Ile Leu Gln
            180                 185                 190

Ala Pro Glu Asn Leu Thr Leu Ser Asn Leu Ser Thr Ser Ile Pro Ser
        195                 200                 205

Val Ser Asn Ala Leu Asn Trp Lys Glu Phe Ser Phe Ile Gln Ser Thr
210                 215                 220

Leu Gly Tyr Val Ile Ile Gln Val Ser Pro Lys Asp Ile Gln Leu Thr
225                 230                 235                 240
```

```
Ile Phe Pro Ser Lys Ser Val Lys Glu Gly Asp Thr Val His Ile His
                245                 250                 255
Arg Ala Gly Gly Leu Phe Val Ala Asp Ala Ile Gln Val Gly Phe Gly
            260                 265                 270
Arg Ile Gly Lys His Phe His Ser Gly Gln Asn His Leu Lys Glu Met
        275                 280                 285
Ala Ile Ser Val Leu Glu Ala Arg Ala Cys Ala Ala Gly Gln Val
    290                 295                 300
Ile Gln Thr Ser Lys Tyr Tyr Met Arg Asp Val Ile Ala Ile Glu Ser
305                 310                 315                 320
Ala Trp Leu Leu Glu Leu Ala Pro Lys Ala Ser Lys Lys Gly Met Trp
                325                 330                 335
Ser Glu Gly Asn Ser Ser His Thr Ile Arg Asp Leu Lys Tyr Thr Ile
            340                 345                 350
Glu Leu Pro Gly Phe Lys Gly Val Lys Gly His Ser Gly Ile Asp Gly
        355                 360                 365
Leu Lys Gly Gln Pro Gly Ala Gln Gly Val Ala Leu Gly Ser Leu Ala
    370                 375                 380
Leu Met Ile Trp Leu Met Thr Thr Pro His Ser His Glu Thr Glu Gln
385                 390                 395                 400
Lys Arg Leu Ser Trp Ile His Cys Trp Lys Tyr Leu Ser Val Gln Ser
                405                 410                 415
Gln Leu Phe Arg Gly Ser Ser Leu Leu Phe Arg Arg Lys Pro Leu Arg
            420                 425                 430
Arg Asn Asn Ser Tyr Thr Ser Tyr Ile Met Ala Ile Cys Gly Met Pro
        435                 440                 445
Leu Asp Ser Phe Arg Glu Val Ala Thr Arg Met Gln Ser Phe Gly Met
    450                 455                 460
Lys Ile Val Gly Tyr Asp Pro Ile Ile Ser Pro Glu Val Ala Thr Val
465                 470                 475                 480
Ser Val Val Ala Leu His Asp Asp Met Glu Asn Gln Pro Leu Ile Gly
                485                 490                 495
Ile Gln Ser Thr Ala Ile Pro Phe Pro Glu Phe Ala Arg Tyr Thr Thr
            500                 505                 510
Pro Glu Asp Thr Thr Pro Glu Pro Gly Glu Asp Pro Arg Val Thr Arg
        515                 520                 525
Gly Tyr Pro Tyr Asp Val Pro Asp Tyr Ala Ser
    530                 535

<210> SEQ ID NO 51
<211> LENGTH: 16
<212> TYPE: PRT
<213> ORGANISM: Artificial Sequence
<220> FEATURE:
<223> OTHER INFORMATION: Generic sequence
<220> FEATURE:
<221> NAME/KEY: MISC_FEATURE
<222> LOCATION: (8)..(8)
<223> OTHER INFORMATION: Xaa is N or S
<220> FEATURE:
<221> NAME/KEY: MISC_FEATURE
<222> LOCATION: (10)..(10)
<223> OTHER INFORMATION: Xaa is D or E
<220> FEATURE:
<221> NAME/KEY: MISC_FEATURE
<222> LOCATION: (12)..(12)
<223> OTHER INFORMATION: Xaa is M or L
<220> FEATURE:
<221> NAME/KEY: MISC_FEATURE
```

-continued

```
<222> LOCATION: (13)..(13)
<223> OTHER INFORMATION: Xaa is G, N, S or T
<220> FEATURE:
<221> NAME/KEY: MISC_FEATURE
<222> LOCATION: (14)..(14)
<223> OTHER INFORMATION: Xaa is K or R
<220> FEATURE:
<221> NAME/KEY: MISC_FEATURE
<222> LOCATION: (16)..(16)
<223> OTHER INFORMATION: Xaa is L or M

<400> SEQUENCE: 51

Gln Ile His Thr Leu Gln Lys Xaa Ser Xaa Arg Xaa Xaa Xaa Gln Xaa
1               5                   10                  15
```